United States Patent
Shumway et al.

(10) Patent No.: US 9,345,705 B2
(45) Date of Patent: May 24, 2016

(54) COMPOSITIONS AND METHODS FOR TREATING CANCER

(75) Inventors: Stuart Denham Shumway, Franklin, MA (US); Carlo Toniatti, Houston, TX (US); Brian Scott Roberts, Huntsville, AL (US); Melissa M. Martin, Thousand Oaks, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/344,190

(22) PCT Filed: Sep. 11, 2012

(86) PCT No.: PCT/US2012/054554
§ 371 (c)(1),
(2), (4) Date: Mar. 11, 2014

(87) PCT Pub. No.: WO2013/039854
PCT Pub. Date: Mar. 21, 2013

(65) Prior Publication Data
US 2014/0343071 A1 Nov. 20, 2014

Related U.S. Application Data

(60) Provisional application No. 61/534,921, filed on Sep. 15, 2011.

(51) Int. Cl.
*A61K 31/519* (2006.01)
*C07D 487/02* (2006.01)
*A61K 31/506* (2006.01)
*A61K 45/06* (2006.01)

(52) U.S. Cl.
CPC ............. *A61K 31/519* (2013.01); *A61K 31/506* (2013.01); *A61K 45/06* (2013.01)

(58) Field of Classification Search
CPC ............................ A61K 31/519; C07D 487/02
USPC ..................... 544/253, 262; 514/258.1, 262.1
See application file for complete search history.

(56) References Cited

U.S. PATENT DOCUMENTS

| 7,196,078 B2 | 3/2007 | Guzi et al. |
| 2010/0124544 A1 | 5/2010 | Kawasaki et al. |
| 2010/0286135 A1 | 11/2010 | Reddy et al. |

FOREIGN PATENT DOCUMENTS

WO 2009151997 A1 12/2009

OTHER PUBLICATIONS

Kurtis D. Davies, P. LouAnn Cable, Jennifer E. Garrus, Francis X. Sullivan, Ira von Carlowitz, Yvan Le Huerou, Eli Wallace, Richard D. Woessner & Stefan Gross (2011) Chk1 inhibition and Wee1 inhibition combine synergistically to impede cellular proliferation, Cancer Biology & Therapy, 12:9, 788-796, DOI: 10.4161/cbt.12.9.17673.*
Prudhomme, M, Novel Checkpoint 1 Inhibitors, Recent Patents on Anti-Cancer Drug Discovery, 2006, 55-68, 1.

* cited by examiner

*Primary Examiner* — Golam M M Shameem
(74) *Attorney, Agent, or Firm* — Richard S. Parr; Catherine D. Fitch

(57) ABSTRACT

The instant invention provides a method of treating a cancer, selected from the group consisting of breast cancer, melanoma, colorectal cancer, non-small cell lung cancer and ovarian cancer, by administering a combination of a WEE1 inhibitor and a CHK1 inhibitor, wherein the WEE1 inhibitor is MK-1775 or a pharmaceutically acceptable salt thereof, or MK-3652 or a pharmaceutically acceptable salt thereof, and the CHK1 inhibitor is MK-8776 or a pharmaceutically acceptable salt thereof, or SCH900444 or a pharmaceutically acceptable salt thereof.

7 Claims, 6 Drawing Sheets

| cell line | MK-1775 EC50 (nM) w/fixed vehicle | MK-1775 EC50 (nM) w/fixed 150 nM MK-8776 | fold change |
|---|---|---|---|
| A2058 | 225 (±10) | 45 (±7) | 5.0 |
| HT-29 | 259 (±107) | 112 (±1) | 2.3 |
| A2780 | 152 (±68) | 82 (±56) | 1.9 |
| LoVo | 109 (±19) | 12 (±11) | 9.1 |
| A427 | 116 (±57) | 54 (±51) | 2.1 |
| SK-MES-1 | 118 (±21) | 27 (±15) | 4.4 |
| NCI-H23 | 102 (±28) | 25 (±19) | 4.1 |

COMPOSITIONS AND METHODS FOR TREATING CANCER

BACKGROUND OF THE INVENTION

Unlike broadly active chemotherapeutics which indescriminately kill dividing cells, select targeted cancer therapeuctics have demonstrated the potential to specifically eradicate cancer cells while sparing "normal" non-cancerous cells, resulting in clinical efficacy and minimized adverse side effects. Nevertheless, most single agent cancer therapies fail in the clinic due to underwhelming anti-tumor responses. Even in the few cases where targeted agent monotherapies have succeeded in treating solid tumors, the effect is usually transient and drug-resistant tumors quickly reemerge. One approach to improve clinical outcome of anti-cancer pharmaceuticals is the combination of two or more therapies, an approach that oncologists have utilized for decades with broadly active DNA-damaging agents. More recently the strategic pairing of targeted oncology agents has gained momentum with the hope of synergistic cytotoxicity, making the combination more effective in treating tumor cells than either single drug alone. Drug combinations are expected to take advantage of synthetic lethality or repressing compensatory feedback mechanisms that would otherwise allow cancer cells to survive effects of monotherapy. Optimal combinations might also delay onset of drug resistance by killing more tumor cells as well as by limiting alternate means of developed cellular resistance.

Small molecule inhibitors against checkpoint kinases constitute a promising class of targeted cancer therapeutics and many are currently under clinical evaluation. CHK1 is an essential serine/threonine kinase involved in two cell cycle checkpoints, the intra-S and G2/M checkpoints. In response to DNA replication stress during S-phase of the cell cycle, CHK1 activity prevents stalled replication forks from collapsing and causing genomic damage (Feijoo, C., et al., *J. Cell Biol.*, 2001; 154(5):913-923). Also, CHK1 activity following DNA damage is necessary for arrest at the G2/M cell cycle boundary, preventing cells from prematurely entering mitosis before damaged DNA has been repaired (O'Connell, M. J., et al., *Embo Journal* 1997, 16(3):545-554; Liu, Q. H., et al., *Genes & Devel.*, 2000, 14(12):1448-1459). Importantly, CHK1 is necessary for unperturbed DNA replication and cell cycle coordination even in the absence of any exogenous insult. As an example, conditional CHK1 heterozygosity leads to aberrant DNA replication, increased DNA damage, and premature mitosis in untreated murine mammary epithelial cells (Lam, M. H., et al., Cancer Cell, 2004, 6(1): 45-59). Several publications describe the cytotoxic nature of CHK1 knockdown or inhibition, either alone or in combination with DNA-damaging therapeutics, demonstrating preclinical proof of concept for CHK1 targeted agents.

WEE1 is an essential tyrosine kinase best recognized as a mitotic gatekeeper that phosphorylates and inactivates cyclin dependent kinase 1 (CDK1=CDC2), the only indispensible human cyclin dependent kinase (Malumbres, M. and Barbacid, M., *Nature Reviews Cancer*, 2009, 9(3):153-166). As cells transition into mitosis, WEE1 activity is reduced, allowing CDK1/cyclin B1 to intiate mitotic events. WEE1 is therefore critical for properly timing cell division in unperturbed cells, and loss of WEE1 results in chromosomal aneuploidy and accumulated DNA damage (Tominaga, Y., et al., *Intl. J. Biol. Sci.*, 2006, 2(4):161-170). Additionally, WEE1 activity can be increased as a result of DNA damage, causing cells to arrest in G2 and allowing for repair of DNA lesions before beginning mitosis (Raleigh, J. M. and O'Connell, M. J., *J. Cell Sci.*, 2000, 113(10):1727-1736). Recently, WEE1 has been shown to be indispensible for genomic integrity specifically as cells traverse S-phase, describing a previously unrecognized role for WEE1 in maintaining fidelity of DNA replication, (Beck, H., et al., *J. Cell Biol.*, 2010, 188(5):629-638). Knockdown of WEE1 by siRNA led to rapid and S-phase specific accumulation of γH2AX, a phosphorylated histone protein that quantitatively represents DNA damage. Interfering with WEE1 has been shown to repress cancer cell proliferation and lead to greater anti-tumor effects of DNA-damaging chemotherapeutics than either single agent alone could achieve.

SUMMARY OF THE INVENTION

The instant invention provides a method of treating a cancer, selected from the group consisting of breast cancer, melanoma, colorectal cancer, non-small cell lung cancer and ovarian cancer, by administering a combination of a WEE1 inhibitor and a CHK1 inhibitor, wherein the WEE1 inhibitor is MK-1775, or a pharmaceutically acceptable salt thereof, or MK-3652, or a pharmaceutically acceptable salt thereof, and the CHK1 inhibitor is MK-8776, or a pharmaceutically acceptable salt thereof, or SCH900444, or a pharmaceutically acceptable salt thereof.

In an embodiment the invention is a method of treating a cancer patient, in need of treatment thereof, comprising administering to said patient a therapeutically effective amount of a WEE1 inhibitor and a CHK1 inhibitor, wherein the WEE1 inhibitor is MK-1775 or a pharmaceutically acceptable salt thereof, or MK-3652 or a pharmaceutically acceptable salt thereof, and the CHK1 inhibitor is MK-8776 or a pharmaceutically acceptable salt thereof, or SCH900444 or a pharmaceutically acceptable salt thereof.

BRIEF DESCRIPTION OF THE DRAWINGS

FIG. 1A: A2058 melanoma cells were treated with a WEE1 inhibitor (MK-1775) for three days in the added presence of a fixed concentration of a CHK1 inhibitor (MK-8776) and response curves were generated from the mean values of growth inhibition. A table representing similar results for other cell lines is shown. FIG. 1B: The reverse experiment from that of FIG. 1A in which MK-8776 was titrated against fixed amounts of MK-1775. FIG. 1C: MK-1775 was not able to potentiate an EC50 potency shift by itself, validating the ability of MK-8776 to potentiate MK-1775.

Figure 4:
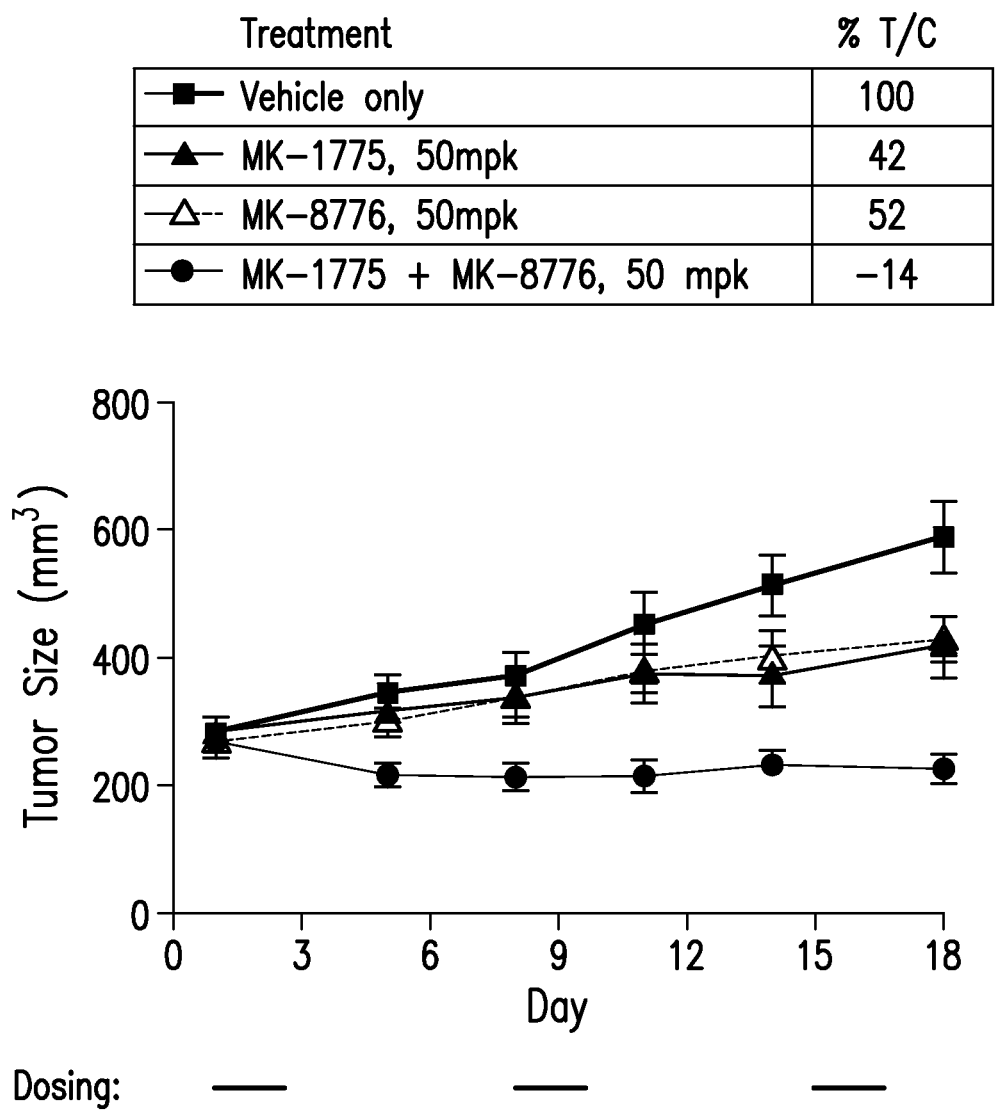

FIG. 4 is a graphic illustrating that combined CHK1 and WEE1 inhibition leads to improved anti-tumor efficacy in a xenograft model of human cancer. LoVo xenograft tumors (n=10 per group) were treated for three weekly cycles, each cycle consisting of twice daily dosing for two days of vehicle, a WEE1 inhibitor (MK-1775) (50 mpk), a CHK1 inhibitor (MK-8776) (50 mpk), or both inhibitors, (MK-1775) (50 mpk) and (MK-8776) (50 mpk). Tumor volumes were measured twice weekly and are represented as the mean±standard deviation.

DETAILED DESCRIPTION OF THE INVENTION

The preclinical studies discussed herein have shown that the combination of a WEE1 inhibitor with a CHK1 inhibitor results in synergistic inhibition of cell proliferation in several human tumor cell lines. Minimal concentrations of the drugs required to block cell proliferation lead to a greater than additive increase of γH2AX, suggesting that the unique combination of a WEE1 and a CHK1 inhibitor disrupts DNA replication and its associated checkpoint. Pharmacodynamic (PD) analysis in xenograft tumors supports this notion, showing an increase in both the percentage of DNA damage containing cells as well as the duration of the DNA damage signal. Consistent with the PD data, the data discussed herein demonstrates that the combination of CHK1 and WEE1 inhibitors leads to regression of a human tumor xenograft model. As such, in vivo, the combination may inhibit cell growth at concentrations as low as 9-fold less than what is required for either agent alone to produce a similar effect. Further, the combination may cause as much as 10-fold higher levels of DNA damage than either single agent alone at similar concentrations. Collectively, these data demonstrate the synergistic anti-tumor effect of co-treatment of a WEE1 and a CHK1 inhibitor, that may result in great benefits for treating human cancer patients.

The present inventors have found that synergistically excellent anticancer activity can be achieved by using a WEE1 inhibitor with a CHK1 inhibitor, specifically, wherein the WEE1 inhibitor is MK-1775 or a pharmaceutically acceptable salt thereof, or MK-3652 or a pharmaceutically acceptable salt thereof, and the CHK1 inhibitor is MK-8776 or a pharmaceutically acceptable salt thereof, or SCH900444 or a pharmaceutically acceptable salt thereof. The invention is especially useful in the treatment of a cancer selected from the group consisting of breast cancer, melanoma, colorectal cancer, non-small cell lung cancer and ovarian cancer. However, the instant invention may prove useful in the treatment of various other cancers, such as, brain cancer, cervicocerebral cancer, soft tissue or bone sarcomas, endometrial cancer, esophageal cancer, thyroid cancer, small cell lung cancer, lung cancer, stomach cancer, gallbladder/bile duct cancer, liver cancer, pancreatic cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, and Hodgkin's lymphoma.

Accordingly, the instant invention relates to a method of treating a cancer, selected from the group consisting of breast cancer, melanoma, colorectal cancer, non-small cell lung cancer and ovarian cancer, with a WEE1 inhibitor and a CHK1 inhibitor, wherein the WEE1 inhibitor is MK-1775, or a pharmaceutically acceptable salt thereof, or MK-3652, or a pharmaceutically acceptable salt thereof, and the CHK1 inhibitor is MK-8776, or a pharmaceutically acceptable salt thereof, or SCH900444, or a pharmaceutically acceptable salt thereof.

In an embodiment of the invention, the WEE1 inhibitor is MK-1775 or a pharmaceutically acceptable salt thereof.

In another embodiment of the invention, the CHK1 inhibitor is MK-8776 or a pharmaceutically acceptable salt thereof.

In an embodiment of the invention, the WEE1 inhibitor is administered in a dose between 100 mg per day and 250 mg per day. In an embodiment of the invention, the WEE1 inhibitor may be dosed twice a day (BID) over the course of two and a half days (for a total of 5 doses) or once a day (QD) over the course of two days (for a total of 2 doses). In an embodiment of the invention, the CHK1 inhibitor is administered in doses from about 100 mg per day to 200 mg per day. In an embodiment of the invention, the CHK1 inhibitor may be dosed once a day (QD) over either one or two days.

The WEE1 inhibitor and the CHK1 inhibitor can be prepared for simultaneous, separate, or successive administration.

Reference to the preferred embodiments set forth above is meant to include all combinations of particular and preferred groups unless stated otherwise. The meanings of the terms used in this description are described below, and the invention is described in more detail hereinunder.

The term "simultaneous" as referred to in this description means that the pharmaceutical preparations of the invention are administered simultaneously in time.

The term "separate" as referred to in this description means that the pharmaceutical preparations of the invention are administered at different times during the course of a common treatment schedule.

The term "successive" as referred to in this description means that administration of one pharmaceutical preparation is followed by administration of the other pharmaceutical preparation; after administration of one pharmaceutical preparation, the second pharmaceutical preparation can be administered substantially immediately after the first pharmaceutical preparation, or the second pharmaceutical preparation can be administered after an effective time period after the first pharmaceutical preparation; and the effective time period is the amount of time given for realization of maximum benefit from the administration of the first pharmaceutical preparation.

The term "cancer" as referred to in this description includes various sarcoma and carcinoma and includes solid cancer and hematopoietic cancer. The solid cancer as referred to herein includes, for example, brain cancer, cervicocerebral cancer, esophageal cancer, thyroid cancer, small cell lung cancer, non-small cell lung cancer, breast cancer, endometrial cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

WEE1 Inhibitors

In an embodiment of the invention, the WEE1 inhibitor of the instant invention is MK-1775, the structure of which as shown below.

MK-1775

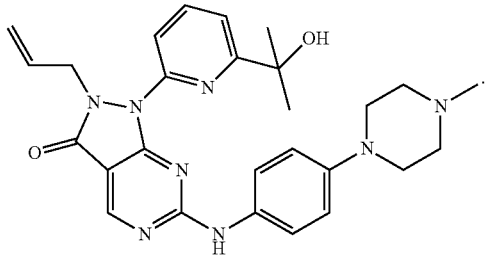

MK-1775 is a WEE1 inhibitor which is useful for the treatment of cancer. MK-1775 is also known as 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one. MK-1775 has been described in U.S. Pat. No. 7,834,019, and in PCT International Publication WO 2007/126122, WO 2007/126128 and WO 2008/153207, which are incorporated by reference herein in their entirety. Crystalline forms of MK-1775 are described in US Publication US2010/0124544 and PCT International Publication WO 2011/034743, which are incorporated by reference herein in their entirety.

In an embodiment of the invention, the WEE1 inhibitor of the instant invention is MK-3652, the structure of which is as shown below.

MK-3652

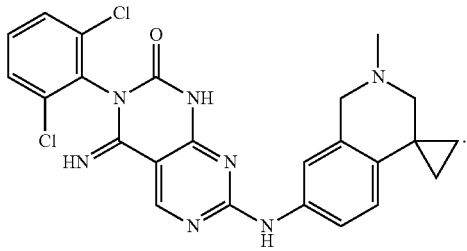

MK-3652 is a WEE1 inhibitor which is useful for the treatment of cancer. MK-3652 is also known as 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. MK-3652 has been described in PCT International Publication WO 2008/153207 and US Publication US2011/0135601, which are incorporated by reference herein in their entirety. Crystalline forms of MK-3652 are described in International Publication WO2009/151997 and US Publication US2011/0092520, which are incorporated by reference herein in their entirety.

CHK1 inhibitors

In an embodiment of the invention, the CHK1 inhibitor of the instant invention is MK-8776, the structure of which is as shown below.

MK-8776

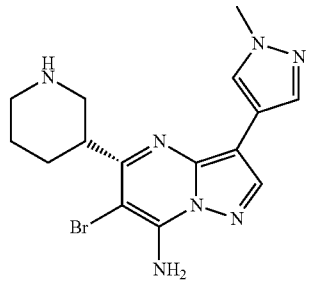

MK-8776 is a CHK1 inhibitor which is useful for the treatment of cancer. MK-8776 is also known as (R)-(−)-6-Bromo-3-(1-methyl-1H-pyrazol-4-yl)-5-piperidin-3-yl-pyrazolo[1,5-a]pyrimidin-7-ylamine, or SCH900776. MK-8776 has been described in U.S. Pat. No. 7,196,078, PCT International Publications WO 2007/044449 and WO 2011/119457, and uses are described in PCT International Publication WO2007/044441, which are incorporated by reference herein in their entirety.

In an embodiment of the invention, the CHK1 inhibitor of the instant invention is SCH900444, the structure of which is as shown below.

SCH900444

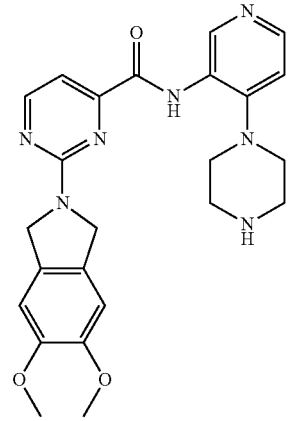

SCH900444 is a CHK1 inhibitor which is useful for the treatment of cancer. SCH900444 is also known as 2-(1,3-dihydro-5,6-dimethoxy-2H-isoindol-2-yl)-N-[4-(1-piperazinyl)-3-pyridinyl]-4-pyrimidinecarboxamide, or SCH1396195. SCH900444 has been described in PCT International Publication WO 2009/014637, which is incorporated by reference herein in its entirety.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

In the compounds described in the present invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds disclosed herein. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds disclosed herein can be prepared without undue experimentation by conventional techniques well known to those skilled in the art or by processes analogous to those described in the Examples herein using appropriate isotopically-enriched reagents and/or intermediates.

The WEE1 and CHK1 inhibitors of the instant invention may also exist as various crystals, amorphous substances, pharmaceutically acceptable salts, hydrates and solvates. Further, the WEE1 and CHK1 inhibitors of the instant invention may be provided as prodrugs. In general, such prodrugs are functional derivatives of the WEE1 inhibitors of the instant invention that can be readily converted into compounds that are needed by living bodies. Accordingly, in the method of treatment of various cancers in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of the compound may include active compounds that are produced by putting the compound in a biological environment, and are within the scope of the compound in the invention.

Dosing and Routes of Administration

With regard to the WEE1 inhibitors and CHK1 inhibitors of the invention, various preparation forms can be selected, and examples thereof include oral preparations such as tablets, capsules, powders, granules or liquids, or sterilized liquid parenteral preparations such as solutions or suspensions, suppositories, ointments and the like. The WEE1 inhibitors and CHK1 inhibitors are available as pharmaceutically acceptable salts. The WEE1 inhibitors and CHK1 inhibitors of the invention are prepared with pharmaceutically acceptable carriers or diluents.

The term "pharmaceutically acceptable salt" as referred to in this description means ordinary, pharmaceutically acceptable salt. For example, when the compound has a hydroxyl group, or an acidic group such as a carboxyl group and a tetrazolyl group, then it may form a base-addition salt at the hydroxyl group or the acidic group; or when the compound has an amino group or a basic heterocyclic group, then it may form an acid-addition salt at the amino group or the basic heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The term "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the mTOR inhibitor, based on the total weight of each preparation.

Liquid preparations are produced in the forms of suspension, syrup, injection and drip infusion (intravenous fluid) using appropriate additives that are conventionally used in liquid preparations, such as water, alcohol, or a plant-derived oil, such as, soybean oil, peanut oil, and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of each preparation.

Liquid preparations such as suspension or syrup for oral administration may contain, for example, 0.1 to 10% by weight of an active ingredient based on the total weight of each preparation.

Each preparation in the invention can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The components of this invention may be administered to mammals, including humans, either alone or, in combination with pharmaceutically acceptable carriers, excipients or diluents, in a pharmaceutical composition, according to standard pharmaceutical practice. The components can be administered orally or parenterally, including the intravenous, intramuscular, intraperitoneal, subcutaneous, rectal and topical routes of administration.

Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved. Further information about suitable dosages is provided below.

The term "administration" and variants thereof (e.g., "administering" a compound) in reference to a component of the invention means introducing the component or a prodrug of the component into the system of the animal in need of treatment. When a component of the invention or prodrug thereof is provided in combination with one or more other active agents (e.g., the WEE1 inhibitor), "administration" and its variants are each understood to include concurrent and sequential introduction of the component or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits a biological or a medicinal response in a tissue, system, animal or human that is being sought by a researcher, veterinarian, medical doctor or other clinician. This includes combination therapy involving the use of multiple therapeutic agents, such as a combined amount of a first and second treatment where the combined amount will achieve the desired biological or medicinal response. The desired biological response can be partial or total inhibition, delay or prevention of the progression of cancer, including cancer metastasis; inhibition, delay or prevention of the recurrence of cancer, including cancer metastasis; or the prevention of the onset or development of cancer (chemoprevention) in a mammal, for example a human.

A suitable amount of a WEE1 inhibitor is administered to a patient undergoing treatment for cancer. In an embodiment, the WEE1 inhibitor is administered in doses from about 100 mg per day to 250 mg per day. In an embodiment of the invention, the WEE1 inhibitor is administered twice daily (BID), over the course of two and a half days, for a total of 5 doses. In another embodiment of the invention, the WEE1 inhibitor is administered once daily (QD) over the course of two days, for a total of 2 doses.

In an embodiment of the invention, the WEE1 inhibitor can be administered 5 times per week. In another embodiment of the invention, the WEE1 inhibitor can be administered 2 times per week.

A suitable amount of a CHK1 inhibitor is administered to a patient undergoing treatment for cancer. In an embodiment, the CHK1 inhibitor is administered in doses from about 100 mg per day to 200 mg per day. In an embodiment of the invention, the CHK1 inhibitor may be dosed once daily (QD) over either one or two days.

In an embodiment of the invention, the CHK1 inhibitor can be administered once a week. In another embodiment of the invention, the WEE1 inhibitor can be administered 2 times per week.

In an embodiment of the invention, the CHK1 inhibitor can be administered once a week. In another embodiment of the invention, the WEE1 inhibitor can be administered 5 times per week.

In an embodiment of the invention, the CHK1 inhibitor can be administered twice a week. In another embodiment of the invention, the WEE1 inhibitor can be administered 2 times per week.

In an embodiment of the invention, the CHK1 inhibitor can be administered twice a week. In another embodiment of the invention, the WEE1 inhibitor can be administered 5 times per week.

In a broad embodiment, the treatment of the present invention involves the combined administration of a WEE1 inhibitor and CHK1 inhibitor. The combined administration includes co administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The WEE1 inhibitor may precede, or follow administration of the CHK1 inhibitor or may be given simultaneously therewith. The clinical dosing of the therapeutic combination of the present invention is likely to be limited by the extent of any adverse reactions.

Additional Indications

In addition to the treatment of breast cancer, melanoma, colorectal cancer, non-small cell lung cancer and ovarian cancer, the WEE1 inhibitor and CHK1 inhibitor combination may also be useful for the treatment of the following cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The WEE1 inhibitor and CHK1 inhibitor combination of the invention may also be useful in treating the following disease states: keloids and psoriasis.

Further included within the scope of the invention is a method of treating or preventing a disease in which angiogenesis is implicated, which is comprised of administering to a mammal in need of such treatment a therapeutically effective amount of the combination of the present invention. Ocular neovascular diseases are an example of conditions where much of the resulting tissue damage can be attributed to aberrant infiltration of blood vessels in the eye (WO 2000/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge, et al., *Expert Opin. Biol. Ther.*, 2002, 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant combination to coat stents and therefore the use of the instant compounds on coated stents for the treatment and/or prevention of restenosis (WO 2003/032809).

Further included within the scope of the instant invention is the use of the instant combination for the treatment and/or prevention of osteoarthritis (WO 2003/035048).

Further included within the scope of the invention is a method of treating hypoinsulinism.

Exemplifying the invention is the use of the WEE1 inhibitor and CHK1 inhibitor combination described above in the preparation of a medicament for the treatment and/or prevention of breast cancer, melanoma, colorectal cancer, non-small cell lung cancer and ovarian cancer.

Additional Anti-Cancer Agents

The WEE1 inhibitor and CHK1 inhibitor combination of the instant invention is also useful in combination with additional therapeutic, chemotherapeutic and anti-cancer agents. Further combinations of the WEE1 inhibitor and CHK1 inhibitor combination of the instant invention with therapeutic, chemotherapeutic and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such additional agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The mTOR inhibitor and $\alpha v\beta 3$ integrin antagonist combination of the instant invention may be particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]- phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (WO 00/50032), Raf kinase inhibitors (such as Bay43-9006) and mTOR inhibitors, such as ridaforolimus, everolimus, temsirolimus, sirolimus or a rapamycin-analog.

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see, for example, U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxy-ethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO 2003/039460, WO 2003/050064, WO 2003/050122, WO 2003/049527, WO 2003/049679, WO 2003/049678, WO 2004/039774, WO 2003/079973, WO 2003/099211, WO 2003/105855, WO 2003/106417, WO 2004/037171, WO 2004/058148, WO 2004/058700, WO 2004/126699, WO 2005/018638, WO 2005/019206, WO 2005/019205, WO 2005/018547, WO 2005/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A., et al., *J. Med. Chem.*, 2003, 46(24):5097-5116.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichloro-phenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; U.S. Pat. Nos. 4,231,938, 4,294,926 and 4,319,039), simvastatin (ZOCOR®; U.S. Pat. Nos. 4,444,784, 4,820,850 and 4,916,239), pravastatin (PRAVACHOL®; U.S. Pat. Nos. 4,346,227, 4,537,859, 4,410,629, 5,030,447 and 5,180,589), fluvastatin (LESCOL®; U.S. Pat. Nos. 5,354,772, 4,911,165, 4,929,437, 5,189,164, 5,118,853, 5,290,946 and 5,356,896), atorvastatin (LIPITOR®; U.S. Pat. Nos. 5,273,995, 4,681,893, 5,489,691 and 5,342,952) and cerivastatin (also known as rivastatin and BAYCHOL®; U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis, see, European J. of Cancer, 1999, 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, 1992, 89:7384; JNCI, 1982, 69:475; Arch. Opthalmol., 1990, 108:573; Anat. Rec., 1994, 238:68; FEBS Letters, 1995, 372:83; Clin. Orthop., 1995, 313:76; J. Mol. Endocrinol., 1996, 16:107; Jpn. J. Pharmacol., 1997, 75:105; Cancer Res., 1997, 57:1625; Cell, 1998, 93:705; Intl. J. Mol. Med., 1998, 2:715; J. Biol. Chem., 1999, 274:9116), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (Fernandez, et al., J. Lab. Clin. Med., 1985, 105:141-145), and antibodies to VEGF (Nature Biotechnology, 1999, 17:963-968); Kim, et al., Nature, 1993, 362:841-844; WO 2000/44777; and WO 2000/61186).

Other therapeutic agents that modulate or inhibit angiogenesis and may also be used in combination with the compounds of the instant invention include agents that modulate or inhibit the coagulation and fibrinolysis systems (Clin. Chem. La. Med., 2000, 38:679-692). Examples of such agents that modulate or inhibit the coagulation and fibrinolysis pathways include, but are not limited to, heparin (Thromb. Haemost., 1998, 80:10-23), low molecular weight heparins and carboxypeptidase U inhibitors (also known as inhibitors of active thrombin activatable fibrinolysis inhibitor [TAFIa]) (Thrombosis Res., 2001, 101:329-354). TAFIa inhibitors have been described in PCT International Publication WO 2003/013526.

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxy-staurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 2001, 411:355-365.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 2002/083064, WO 2002/083139, WO 2002/083140, US 2004/0116432, WO 2002/083138, US 2004/0102360, WO 2003/086404, WO 2003/086279, WO 2003/086394, WO 2003/084473, WO 2003/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, WO 2006/135627, WO 206/091395, WO 2006/110638), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

Specific anti-IGF-1R antibodies include, but are not limited to, dalotuzumab, figitumumab, cixutumumab, SHC 717454, Roche R1507, EM164 or Amgen AMG479.

As described above, the combinations with NSAID's are directed to the use of NSAID's which are potent COX-2 inhibiting agents. For purposes of this specification an NSAID is potent if it possesses an IC50 for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823,U.S. Pat. No. 5,633, 272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-643-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the mTOR inhibitor and $\alpha v\beta 3$ integrin antagonist combination of the instant invention with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (*J. Cardiovasc. Pharmacol.*, 1998, 31:909-913; *J. Biol. Chem.*, 1999, 274: 9116-9121; *Invest. Ophthalmol. Vis. Sci.*, 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.*, 2001, 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer, see, Hall, et al., *Am. J. Hum. Genet.*, 1997, 61:785-789 and Kufe, et al., *Cancer Medicine*, 5th Ed, B. C. Decker, Hamilton, 2000, pp 876-889. Gene therapy can be used to deliver any tumor suppressing gene. Examples of such genes include, but are not limited to, p53, which can be delivered via recombinant virus-mediated gene transfer (U.S. Pat. No. 6,069,134), a uPA/uPAR antagonist (*Gene Therapy*, 1998, 5(8):1105-1113), and interferon gamma (*J. Immunol.*, 2000, 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

The WEE1 inhibitor and CHK1 inhibitor combination of the instant invention may also be administered with an agent useful in the treatment of anemia. Such an anemia treatment agent is, for example, a continuous eythropoiesis receptor activator (such as epoetin alfa).

The WEE1 inhibitor and CHK1 inhibitor combination of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

The WEE1 inhibitor and CHK1 inhibitor combination of the instant invention may also be administered with an immunologic-enhancing drug, such as levamisole, isoprinosine and Zadaxin.

The WEE1 inhibitor and CHK1 inhibitor combination of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

The WEE1 inhibitor and CHK1 inhibitor combination of the instant invention may also be useful for treating or preventing breast cancer in combination with aromatase inhibitors. Examples of aromatase inhibitors include but are not limited to: anastrozole, letrozole and exemestane.

The WEE1 inhibitor and CHK1 inhibitor combination of the instant invention may also be useful for treating or preventing cancer in combination with siRNA therapeutics.

The WEE1 inhibitor and CHK1 inhibitor combination of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539, WO 02/47671 (including LY-450139) and US 2005/075320.

The WEE1 inhibitor and CHK1 inhibitor combination of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, o 2006/135627, WO 2006/091395, WO 2006/110638.

The WEE1 inhibitor and CHK1 inhibitor combination of the instant invention may also be useful for treating or preventing cancer in combination with PARP inhibitors.

Radiation therapy itself means an ordinary method in the field of treatment of cancer. For radiation therapy, employable are various radiations such as X-ray, γ-ray, neutron ray, electron beam, proton beam; and radiation sources. In a most popular radiation therapy, a linear accelerator is used for irradiation with external radiations, γ-ray.

The WEE1 inhibitor and CHK1 inhibitor combination of the instant invention may also be useful for treating cancer in further combination with the following therapeutic agents: abarelix (Plenaxis Depot®); abiraterone acetate (Zytiga®); (Actiq®); aldesleukin (Prokine®); Aldesleukin (Proleukin®); Alemtuzumab (Campath®); alfuzosin HCl (UroXatral®); alitretinoin (Panretin®); allopurinol (Zyloprim®); altretamine (Hexalen®); amifostine (Ethyol®); anastrozole (Arimidex®); (Anzemet®); (Anexsia®); aprepitant (Emend®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); (Brofenac®); busulfan intravenous (Busulflex®); busulfan oral (Myleran®); cabazitaxel (Jevtana®); calusterone (Methosarb®); capecitabine (Xeloda®); carboplatin (Paraplatin®); carmustine (BCNU®, BiCNU®); carmustine carmustine with Polifeprosan 20 Implant (Gliadel Wafer®); celecoxib (Celebrex®); cetuximab (Erbitux®); chlorambucil (Leukeran®); cinacalcet (Sensipar®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); decitabine (Dacogen®); degarelix (Degarelix®); Denileukin diftitox (Ontak®); denosumab (Xgeva®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); eribulin mesylate (Halaven®); erlotinib (Tarceva®); estramustine (Emcyt®); etoposide phosphate (Etopophos®); etoposide, VP-16 (Vepesid®); everolimus (Afinitor®); exemestane (Aromasin®); fentanyl buccal (Onsolis®); fentanyl citrate (Fentora®); fentanyl sublingual tablets (Abstral®); Filgrastim (Neupogen®); floxuridine (intraarterial) (FUDR®); fludarabine (Fludara®); fluorouracil, 5-FU (Adrucil®); flutamide (Eulexin®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); granisetron (Kytril Solution®) (Sancuso®); histrelin acetate (Histrelin Implant®); human papillomavirus bivalent vaccine (Cervarix®); hydroxyurea (Hydreag); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); ipilimumab (Yervoy®); irinotecan (Camptosar®); (Kadian®); ixabepilone (Ixempra®); lapatinib (Tykerb®); lenalidomide (Revlimid®); letrozole (Femara®); leucovorin (Wellcovorin®, Leucovorin®); Leuprolide Acetate (Eligard®); (Lupron Depot®); (Viadur®); levamisole (Ergamisol®); levoleucovorin (Fusilev®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50®); nelarabine (Arranon®); nilotinib hydrochloride monohydrate (Tasigna®); Nofetumomab (Verluma®); ofatumumab (Arzerra®); ondansetron (Zuplenz®); Oprelvekin (Neumega®); (Neupogen®); oxaliplatin (Eloxatin®); paclitaxel (Paxene®); paclitaxel (Taxol®); paclitaxel protein-bound particles (Abraxane®); palifermin (Kepivance®); palonosetron (Aloxi®); pamidronate (Aredia®); panitumumab (Vectibix®); pazopanib (Votrient®); pegademase (Adagen (Pegademase Bovine)®); pegaspargase (Oncaspar®); Pegfilgrastim (Neulasta®); peginterferon alfa-2B (Sylatron®); pemetrexed disodium (Alimta®); pentostatin (Nipent®); pipobroman (Vercyte®); plerixafor injection (Mozobil®); plicamycin, mithramycin (Mithracin®); porfimer sodium (Photofrin®); pralatrexate injection (Folotyn®); procarbazine (Matulane®); (Quadramet®); quadrivalent human papillomavirus (types 6, 11, 16, 18) recombinant vaccine (Gardasil®); quinacrine (Atabrine®); raloxifene hydrochloride (Evista®); Rasburicase (Elitek®); Rituximab (Rituxan®); romidepsin (Istodax®); sargramostim (Leukine®); Sargramostim (Prokine®); secretin (SecreFlo®); sipuleucel-T (Provenge®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); (Temodar®); testolactone (Teslac®); thalidomide (Thalomid®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); (Trelstar LA®); tretinoin, ATRA (Vesanoid®); triptorelin pamoate (Trelstar Depot®); (UltraJect®); Uracil Mustard (Uracil Mustard Capsules®); valrubicin (Valstar®); vandetanib (Vandetanib®); vinblastine (Velban®); vincristine (Oncovin®); vinorelbine (Navelbine®); vorinostat (Zolinza®); (Zofran ODT®); and zoledronate (Zometa®).

All patents, publications and pending patent applications identified are hereby incorporated by reference as if set forth at length.

The abbreviations used herein have the following tabulated meanings. Abbreviations not tabulated below have their meanings as commonly used unless specifically stated otherwise.

| | |
|---|---|
| ACN | Acrylonitrile |
| $CHCl_3$ | Chloroform |
| $CH_2Cl_2$ | Dichloromethane |
| $CH_3CN$ | Acetonitrile |
| DCM | Dichloromethane |
| DIEA | Diisopropylethylamine |
| DME | Dimethyl ether |
| DMF | Dimethylformamide |
| $Et_3N$ | Triethylamine |
| $Et_2O$ | Diethyl ether |
| EtOAc | Ethyl acetate |
| EtOH | Ethanol |
| HOAc | Acetic acid |
| HATU | 2-(7-Aza-1H-benzotriazole-1-yl)-1,1,3,3-tetramethyluronium hexafluorophosphate |
| LiHMDS | Lithium bis(trimethylsilyl)amide |
| MeOH | Methanol |
| $MgSO_4$ | Magneisium sulfate |
| $NaHCO_3$ | Sodium bicarbonate |
| $NaNO_2$ | Sodium nitrite |
| NaOH | Sodium hydroxide |
| $Na_2SO_4$ | Sodium sulfate |
| NBS | N-Bromosuccinimide |
| $POCl_3$ | Phosphoryl chloride |
| TEA | Triethylaluminium |
| TFA | Trifluoroacetic Acid |
| THF | Tetrahydrofuran |

The WEE1 and CHK1 inhibitors of the instant invention can be prepared according to the following examples, using appropriate materials. The specific anticancer agents illustrated in the examples are not, however, to be construed as forming the only genus that is considered as the invention. The illustrative Examples below, therefore, are not limited by the anticancer agents listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

EXAMPLES

Example 1

Preparation of MK-1775

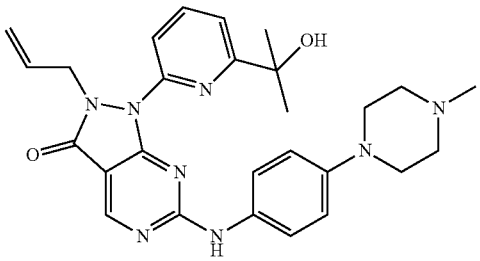 [SMILES: C=CCn1c(=O)c2cnc(Nc3ccc(N4CCN(C)CC4)cc3)nc2n1-c1cccc(C(C)(C)O)n1]

Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one Step 1) Production of 2-(6-bromo-2-pyridinyl)-2-propanol In a nitrogen atmosphere, 30 mL of 3 M methylmagnesium iodide/diethyl ether was added to 300 mL of diethyl ether solution of 8.72 g of methyl 6-bromopyridine-2-carboxylate. Water and 2N hydrochloric acid were added to the reaction liquid, and extracted with ethyl acetate. This was washed with aqueous saturated sodium hydrogencarbonate solution and saturated saline water, and dried with anhydrous magnesium sulfate. The solvent was evaporated away under reduced pressure to obtain 8.51 g of crude 2-(6-bromo-2-pyridinyl)-2-propanol as a yellow oily substance. $^1$H-NMR (400 MHz, CDCl3) δ: 7.56 (1H, t, J=7.8 Hz), 7.38 (1H, dd, J=7.8, 1.0 Hz), 7.36 (1H, dd, J=7.8, 1.0 Hz), 1.55 (6H, s). ESI-MS Found: m/z [M+H]+ 216, 218.

Step 2) Production of 2-allyl-1-[6-(1-hydroxy-1-methylethyl)-2-pyridinyl]-6-(methylthio)-1,2-dihydro-3H-pyrazolo[3,4-d]pyrimidin-3-one 12.89 g of the entitled compound was obtained in the same manner as in Preparative Example 1-1, for which, however, the compound obtained in the above reaction was used in place of 2-iodopyridine used in Preparative Example 1-1. $^1$H-NMR (400 MHz, CDCl$_3$) δ: 8.95 (1H, s), 7.91 (1H, t, J=8.0 Hz), 7.76 (1H, d, J=7.3 Hz), 7.40 (1H, dd, J=7.8, 1.0 Hz), 5.70 (1H, ddt, J=17.1, 10.2, 6.3 Hz), 5.06 (1H, dd, J=10.2, 1.0 Hz), 4.93 (1H, dd, J=17.1, 1.2 Hz), 4.81 (2H, d, J=6.3 Hz), 2.59 (4H, s), 1.59 (6H, s). ESI-MS Found: m/z [M+H]+:358.

Step 3) Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one 817 mg of m-chloroperbenzoic acid (>65%) was added to toluene (20 mL) solution of 1.10 g of the above produce, and stirred for 20 minutes. 1.61 mL of N,N-diisopropylethylamine and 706 mg of 4-(4-methylpiperazin-1-yl)aniline were added to the reaction liquid, and stirred overnight. Aqueous saturated sodium hydrogencarbonate solution was added to the reaction liquid, extracted with ethyl acetate, washed with saturated saline water, and dried with anhydrous magnesium sulfate. The solvent was evaporated away, and the residue was purified through basic silica gel column chromatography (hexane/ethyl acetate=1/1 to 0/1, ethyl acetate/ethanol=98/2). After concentrated, this was recrystallized from ethyl acetate to obtain 1.20 g of the entitled compound as a yellow solid. $^1$H-NMR (400 MHz, CDCl$_3$) δ: 8.83 (1H, s), 7.86 (1H, dd, J=8.0, 7.8 Hz), 7.75 (1H, d, J=7.3 Hz), 7.49 (1H, brs), 7.48 (2H, d, J=9.0 Hz), 7.34 (1H, d, J=7.4 Hz), 6.93 (2H, d, J=9.0 Hz), 5.70 (1H, ddt, J=17.2, 10.0, 6.5 Hz), 5.04 (1H, d, J=10.0 Hz), 4.94 (1H, d, J=17.2 Hz), 4.74 (2H, d, J=6.5 Hz), 3.26 (4H, t, J=4.8 Hz), 2.73 (4H, brs), 2.44 (3H, s), 1.59 (6H, s). ESI-MS Found: m/z [M+H]+ 501.

Preparative Example 1-1

Production of 2-allyl-6-(methylthio)-1-pyridin-2-yl-3H-pyrazolo[3,4-d]pyrimidin-3-one 2.4 mL of N,N'-dimethylethylenediamine was added to 1,4-dioxane (50 mL) solution of 4.44 g of 2-allyl-6-(methylthio)-1,2-dihydro-3H-pyrazolo[3,4-d]pyrimidin-3-one, 3.80 g of copper(I) iodide, 5.33 g of 2-iodopyridine and 3.80 g of potassium carbonate, and stirred overnight at 95° C. The reaction liquid was cooled, aqueous ammonia was added thereto and extracted with ethyl acetate, washed with saturated saline water and dried with anhydrous magnesium sulfate. The solvent was evaporated away under reduced pressure, and crystallized with ethyl acetate to obtain 5.15 g of the entitled compound as a white solid. $^1$H-NMR (400 MHz, CDCl3) δ: 8.94 (1H, s), 8.52 (1H, d, J=5.1 Hz), 7.90 (2H, d, J=3.5 Hz), 7.29-7.25 (1H, m), 5.68 (1H, ddt, J=17.0, 10.2, 6.3 Hz), 5.05 (1H, d, J=10.2 Hz), 4.91 (1H, d, J=17.0 Hz), 4.85 (1H, d, J=6.3 Hz), 2.58 (3H, s).

Example 2

Preparation of MK-8776

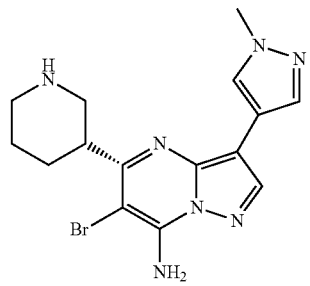

Production of (R)-(−)-6-Bromo-3-(1-methyl-1H-pyrazol-4-yl)-5-piperidin-3-yl-pyrazolo[1,5-a]pyrimidin-7-ylamine Preparative Example 2-1

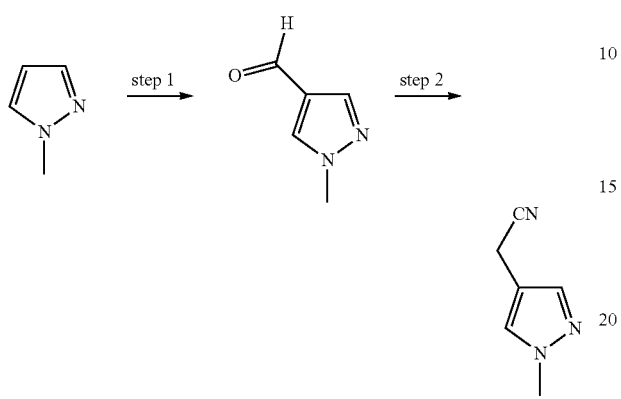

Step 1) Method A: Phosphorus oxychloride (6.92 g, 45.1 mmol, 1.5 eq.) was cooled to 0° C. and then added drop-wise to anhydrous DMF (3.50 mL, 45.2 mmol, 1.5 eq.) at 0° C. The colorless DMF solution soon becomes orange. The mixture was stirred for 1 hour at room temperature and then heated to 80° C. 1-Methyl-1H-pyrazole (2.5 mL, 30.2 mmol) is then added drop-wise to the reaction, and the resulting mixture was stirred 3 hours at 95° C. The reaction was then quenched by slow addition to ice (40 g) via Pasteur pipette. The pH of the resulting solution was 2, and it was raised to 5 by slowly adding 12N aqueous sodium hydroxide solution (11.2 mL total). The resulting aqueous solution was extracted with dichloromethane (3×40 mL). At this point, the pH of the aqueous layer had dropped to 3, therefore additional 12 N NaOH solution (1 mL) was added to bring the pH to 6. The aqueous layer was then extracted further with ether (4×40 mL). The combined extracts were then dried over sodium sulfate, filtered and concentrated (at about 40-50° C.). After drying for 30 minutes under vacuum, a brown oil was recovered (3.79 g) which NMR indicated consisted of a mixture of product, starting material and DMF (52 wt %, 22 wt %, and 26 wt %, respectively). The calculated yield of was 59% and the calculated yield for recovery of unreacted starting material, was 34%. This crude material may be used without further purification in the next step.

Method B: Phosphorus oxychloride (46.7 g, 304.51 mmol, 1.0 eq.) was added dropwise to a stirred solution of 1-methyl-1H-pyrazole (25 g, 304.51 mmol) at 0° C. in anhydrous DMF (62 mL, 800.69 mmol, 2.63 eq.). The solution was then heated to 100° C. and stirred for 2.5 hours. After cooling, the reaction was quenched with ice-water (400 mL), basified with aqueous sodium hydroxide solution to pH 8, and extracted with dichloromethane (4×1 L). The combined extracts were dried over sodium sulfate, filtered and concentrated to give a brown oil (32 g). This was then partially purified by silica gel chromatography eluting with ether followed by 95% ether-ethyl acetate to yield a yellow oil (23 g) containing 7 wt % DMF. Step 2) Potassium t-butoxide (23.47 g, 199.1 mmol, 2.44 eq.) was suspended in anhydrous DME (90 mL) and cooled to −60° C. Tosyl methyl isocyanide (23.76 g, 121.7 mmol, 1.49 eq.) was dissolved in anhydrous DME (75 mL) and the solution was added drop-wise to the potassium t-butoxide solution over 20 minutes. After stirring for 20 minutes between −60 and −55° C., the aldehyde from Step 1 in anhydrous DME (55 mL) was added over 23 minutes. The reaction was stirred for one hour at −55 to −50° C., and then methanol (90 mL) was added. The cooling bath was removed, and after stirring for 5 minutes in air, the reaction flask was immersed in an oil bath preheated to 85° C. The reaction was stirred for 1 hour. After cooling, the mixture was concentrated and the resulting tan solid was dissolved in water (180 mL) with acetic acid (9 mL). This was extracted with ethyl acetate (3×250 mL), and these extracts were combined, washed with brine (100 mL), dried over sodium sulfate, filtered and concentrated to yield a brown oil (13.71 g). This oil was dissolved in dichloromethane and purified by silica-gel chromatography using a gradient from 0% to 15% dichloromethane-acetone to yield a bright yellow oil in 63% yield (7.89 g).

Preparative Example 2-2

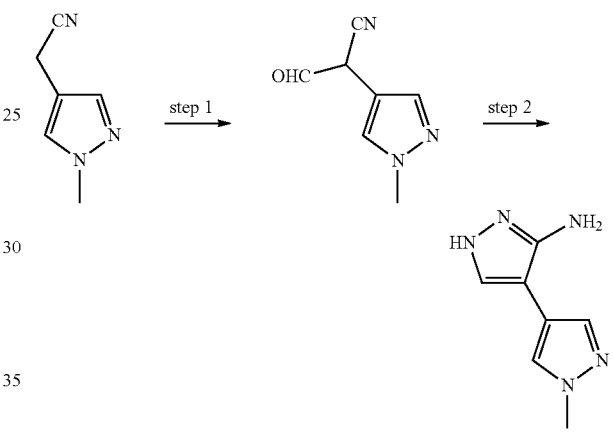

Step 1) The compound from Preparative Example 2-1 (8.00 g, 66.17 mmol) and ethyl formate (11.3 mL, 139.9 mmol, 2.11 eq.) were dissolved in anhydrous DME (35 mL) and added drop-wise to a suspension of potassium-t-butoxide (11.88 g of 95%, 100.77 mmol, 1.52 equiv.) in anhydrous DME (85 mL) in an open pressure tube. After addition was complete, the tube was sealed and stirred at 85° C. for 18 hours. After cooling, the resulting thick suspension was diluted with water (300 mL) to yield a solution of pH 8, and was extracted with ethyl acetate (3×300 mL). These extracts were discarded, and the aqueous solution was then acidified to pH 4 with 8N aqueous hydrochloric acid (2 mL) resulting in the formation of a white precipitate. This suspension was extracted with ethyl acetate (3×700 mL). The combined extracts were washed with brine, dried with sodium sulfate, filtered and concentrated to yield a yellow-white solid (8.98 g, 93% yield).

Step 2) The formyl acetonitrile from Step 1 (10.97 g, 73.63 mmol) was suspended in absolute ethanol (400 mL), and hydrazine monohydrochloride (10.67 g, 156 mmol, 2.12 equiv.) was then added. The mixture was stirred 15 hours at 90° C. to yield an orange solution with a large amount of a fine yellow precipitate. After briefly allowing the reaction to cool, 7N ammonia/methanol (25 mL, 175 mmol) was added and the mixture was stirred for 20 minutes. The mixture was filtered to remove the precipitated solid. The filtrate solution was then concentrated to yield a yellow-white solid weighing 17.70 g. This solid was then loaded dry on a chromatography column and purified eluting with 10% methanol-dichloromethane (5 volumes) followed by 10% to 15% 7N-ammonia/methanol-dichloromethane (7 volumes) to yield an off-white solid (11.35 g, 95% yield). $^1$H NMR (DMSO-d$_6$): δ 11.4 (s, 1H), 7.76 (s, 1H), 7.54 (s, 1H), 7.48 (s, 1H), 4.54 (s, 2H), 3.79 (s, 3H).

Preparative Example 2-3

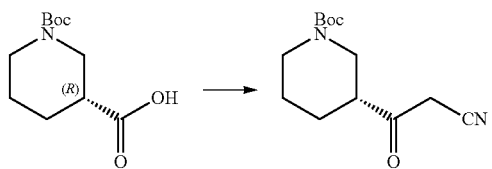

Step 1) A solution of N-Boc-(R)-nipecotic acid (2.0 g, 8.72 mmol) in THF (26 mL) was treated with 1,1'-carbonyldiimidazole (1.41 g, 1.0 equiv.). The solution was stirred at 25° C. for 18 hours. Saturated NaCl (50 mL) was added. The aqueous layer was extracted with Et$_2$O (3×25 mL). The Et$_2$O layer was washed with a 5% aqueous NaHCO$_3$ solution (50 mL) and saturated NaCl (50 mL). The organic layer was dried (MgSO$_4$), filtered and concentrated under reduced pressure to provide the product (2.2 g, 90.7%) as a white solid.

Step 2) A solution of LiHMDS (15.8 mL of a 1.0M solution in THF, 2.0 equiv.) in THF (24 mL) was cooled to −78° C. and treated with CH$_3$CN (0.83 mL, 2.0 equiv.) dropwise. The solution was stirred at −7° C. for 1 hour. To this solution was added the solution of acyl imidazole from Step 1 (2.2 g) in THF (24 mL) dropwise over 10 minutes. The solution was stirred at −78° C. for 0.5 hour and quenched by the addition of saturated NH$_4$Cl (100 mL). The aqueous layer was extracted with Et$_2$O (3×50 mL). The combined organic layer was dried (Na$_2$SO$_4$), filtered and concentrated under reduced pressure. Purification by an Analogix purification system using a RediSep 40 g column (0-50% ethyl acetate-hexanes gradient) afforded the product (1.25 g, 63%) as a pale yellow oil.

Preparative Example 2-4

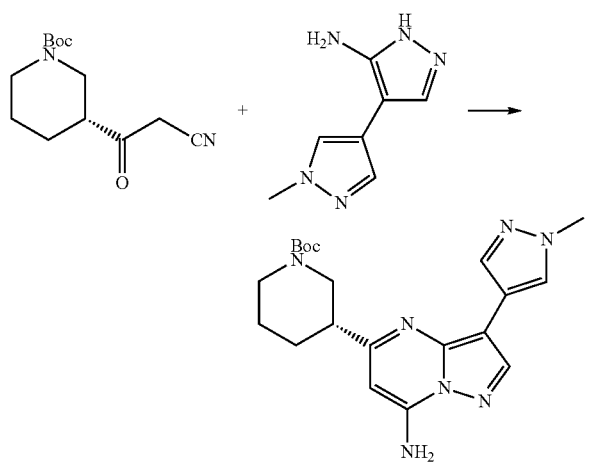

A solution of the compound from Preparative Example 2-3 (0.23 g, 0.93 mmol) and the compound from Preparative Example 2-2 (0.12 g, 1.0 equiv.) in EtOH (0.37 mL) was heated at 45° C. for 18 hours. The solution was cooled to 25° C. Preparative thin layer chromatography (20% acetone-CH$_2$Cl$_2$) afforded the product (0.26 g, 70%) as a white solid.

Preparative Example 2-5

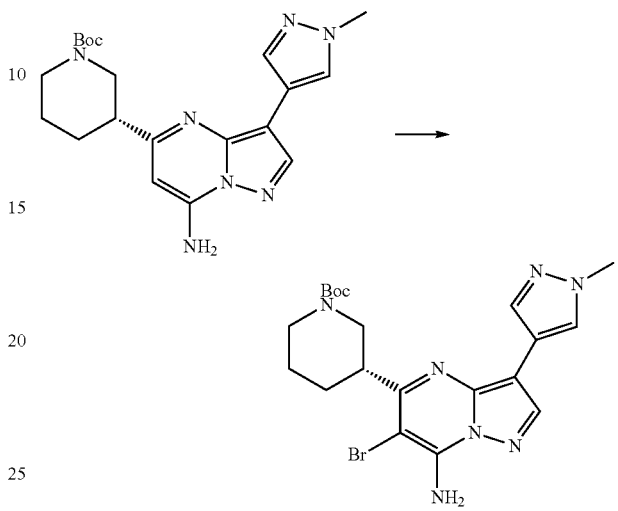

To a solution of the compound from Preparative Example 2-4 (0.79 g, 1.0 equiv.) in CH$_3$CN/CH$_2$Cl$_2$ (10 mL, 1:1) was added a solution of NBS (0.34 mg, 0.95 equiv.) in CH$_3$CN (2 mL) over 10 minutes. When TLC analysis showed complete consumption of starting material, the mixture was concentrated under reduced pressure. The crude product was dissolved in CHCl$_3$ and washed sequentially with H$_2$O (3×3 mL) and brine (1×3 mL). The organic layer was dried over Na$_2$SO$_4$, filtered and concentrated under reduced pressure to afford a light orange solid (0.92 g, 96% yield). LCMS: M$^+$=476.

Preparative Example 2-6

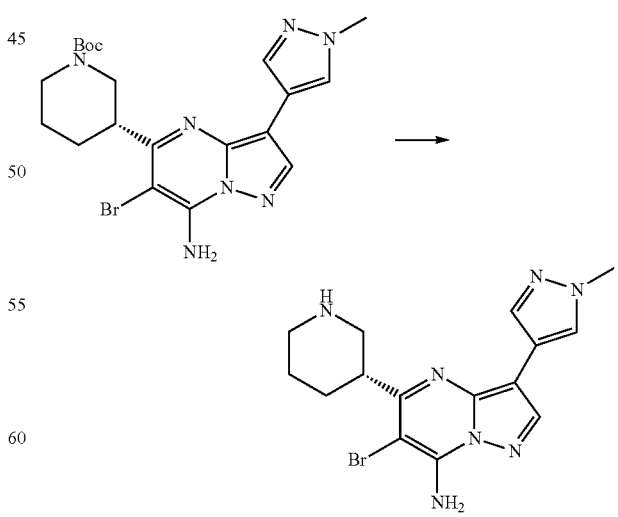

To a solution of the compound from Preparative Example 2-5 (1.0 g, 1.0 equiv.) in CH$_2$Cl$_2$ (20 mL) at 0° C. was added TFA dropwise. The solution was stirred at 0° C. for 30 minutes and warmed to room temperature for 15 minutes. The mixture was concentrated under reduced pressure adding several portions of $CH_2Cl_2$ to azeotrope trace TFA. The resulting oil was dried under high vacuum for 1 hour and treated with 7M $NH_3$ in MeOH (50 mL) and stirred for 4 hours at room temperature. The resulting solution was concentrated under reduced pressure and the crude product purified by Analogix BSR pump using a 40 g Isco column on 35% speed using a gradient of 20:1 $CH_2Cl_2$/MeOH to 40:1 $CH_2Cl_2$/7M $NH_3$ in MeOH to 20:1 $CH_2Cl_2$/7M $NH_3$ in MeOH to afford pure product. LCMS: $M^+$=376

Example 3

Preparation of MK-3652

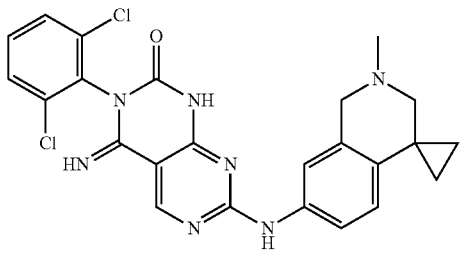 [SMILES: CN1Cc2cc(Nc3ncc4c(=N)n(-c5c(Cl)cccc5Cl)c(=O)[nH]c4n3)ccc2C2(CC2)C1]

Production of 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one A 1-butanol solution of 1.5 g of 7-chloro-3-(2,6-dichlorophenyl)-4-imino-3,4-dihydropyrimido[4,5-d]pyrimidin-2(1H)-one obtained in Preparative Example 3-1, 1 g of 2'-methyl-2',3'-dihydro-1'H-spiro[cyclopropane-1,4'-isoquinolin]-7'-amine obtained in Preparative Example 3-2, and 0.83 g of p-toluenesulfonic acid monohydrate was stirred at 90° C. for 15 minutes. The reaction liquid was cooled, then diluted with chloroform, and the organic layer was washed with aqueous saturated sodium bicarbonate solution and then saturated saline water, and dried with anhydrous magnesium sulfate, filtered, and the solvent was evaporated away. Thus obtained, the roughly-purified product was purified through basic silica gel column chromatography to obtain 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one. This was dissolved in a mixed solvent of chloroform/methanol, and 1.5 equivalents of aqueous hydrochloric acid solution was added thereto, and stirred at room temperature for 5 minutes. Then, the solvent was evaporated away, and the residue was washed with ethyl acetate to obtain 1.5 g (yield, 64%) of 3-(2,6-dichlorophenyl)-4-imino-7-[(2'-methyl-2',3'-dihydro-1'H-spiro [cyclopropane-1,4'-isoquinolin]-7'-yl)amino]-3,4-dihydropyrimido[4,5-d]pyrimidin-2(1H)-one dihydrochloride as a yellow solid. $^1$H-NMR (400 MHz, DMSO-$d_6$) δ: 11.83 (1H, brs), 10.05 (1H, brs), 9.10 (1H, s), 8.88 (1H, s), 7.79-7.68 (1H, m), 7.63-7.59 (2H, m), 7.47 (1H, t, J=8.2 Hz), 7.38 (1H, d, J=8.3 Hz), 6.63 (1H, d, J=8.5 Hz), 3.59 (2H, s), 2.44 (2H, s), 2.32 (3H, s), 0.90-0.81 (4H, m) ESI-MS Found: m/z [M+H]+ 494.

Preparative Example 3-1

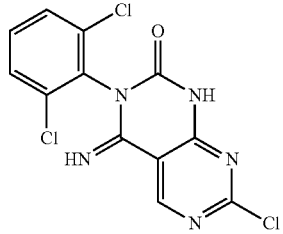 [SMILES: N=c1c2cnc(Cl)nc2[nH]c(=O)n1-c1c(Cl)cccc1Cl]

Production of 7-chloro-3-(2,6-dichlorophenyl)-4-imino-3,4-dihydropyrimido[4,5-d]pyrimidin-2(1H)-one 1.12 g of sodium hydride was added to an N,N-dimethylformamide (35 mL) solution of 3.0 g of 4-amino-2-chloropyrimidine-5-carbonitrile, and stirred at room temperature for 5 minutes. 4.38 g of 2,6-dichlorophenyl isocyanate was added to the reaction liquid, and stirred at room temperature for 1 hour. Ethyl acetate and aqueous 1 N hydrochloric acid solution were added to the reaction solution, and the organic layer was separated. This was washed with saturated saline water, dried with anhydrous magnesium sulfate, and the solvent was evaporated away. The precipitated solid was solidified with a mixed solvent of methanol/ethyl acetate and taken out through filtration to obtain 3.8 g of the entitled compound as a white solid. $^1$H-NMR (400 MHz, DMSO-$d_6$) δ: 9.33 (1H, s), 7.66 (2H, d, J=8.2 Hz), 7.53 (1H, t, J=8.2 Hz) ESI-MS Found: m/z [M+H] 342.

Preparative Example 3-2

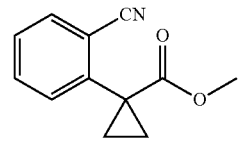

Production of 2'-methyl-2',3'-dihydro-1'H-spiro[cyclopropane-1,4'-isoquinolin]-7'-amine Step 1) Production of methyl 1-(2-cyanophenyl)cyclopropanecarboxylate 1.5 g of tetra-n-butylammonium bromide, 6.5 g of 1,2-dibromoethane and 20 mL of aqueous 50% sodium hydroxide solution were added to a toluene (40 mL) solution of 4.0 g of methyl 2-cyanophenylacetate, and stirred at room temperature for 1 hour. Water was added to the reaction liquid, and extracted with ethyl acetate. The organic layer was washed with saturated saline water, dried with anhydrous magnesium sulfate, and the solvent was evaporated away under reduced pressure. The crude product was purified through silica gel column chromatography (hexane/ethyl acetate) to obtain 3.0 g of the entitled compound as a colorless compound.
¹H-NMR (400 MHz, CDCl$_3$) δ: 7.66 (1H, dd, J=7.6, 1.2 Hz), 7.55 (1H, td, J=7.6, 1.2 Hz), 7.43-7.36 (2H, m), 3.66 (3H, s), 1.82 (2H, q, J=3.7 Hz), 1.30 (2H, q, J=3.7 Hz) ESI-MS Found: m/z [M+H] 202.

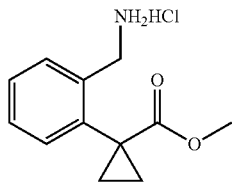

Step 2) Production of methyl 1-[2-(aminomethyl)phenyl]cyclopropanecarboxylate monohydrochloride 1.6 g of 10% palladium-carbon was added to an ethanol (50 mL) solution of 2.95 g of the compound obtained in the above reaction Step 1), and stirred in a hydrogen atmosphere under 2 atmospheric pressure at room temperature for 3 hours. The palladium-carbon was removed through filtration, the filtrate was concentrated under reduced pressure, and the crude product was washed with diethyl ether to obtain 3.2 g of the entitled compound as a colorless solid.

¹H-NMR (DMSO-d$_6$) δ: 8.47 (2H, s), 7.55 (1H, d, J=6.8 Hz), 7.38 (3H, td, J=7.2, 2.1 Hz), 7.36-7.29 (2H, m), 4.04 (2H, d, J=4.9 Hz), 3.54 (3H, s), 1.61-1.56 (2H, m), 1.33-1.29 (2H, m) ESI-MS Found: m/z [M+H] 206.

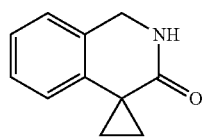 [SMILES: O=C1NCc2ccccc2C12CC2]

Step 3) Production of 1',2'-dihydro-3'H-spiro[cyclopropane-1,4'-isoquinolin]-3'-one 4 mL of aqueous 5 N sodium hydroxide solution was added to a methanol (50 mL) solution of 3.2 g of the compound obtained in the above reaction Step 2), and stirred at room temperature for 30 minutes. This was neutralized with aqueous 1 N hydrochloric acid added thereto, and methanol was evaporated away under reduced pressure. The residue was diluted with water, and extracted three times with ethyl acetate. The organic layer was washed with saturated saline water, dried with anhydrous magnesium sulfate, and the solvent was evaporated away under reduced pressure to obtain 2.1 g of the entitled compound as a colorless solid. ¹H-NMR (CDCl$_3$) δ: 7.23 (1H, td, J=7.8, 1.1 Hz), 7.18 (1H, td, J=7.3, 1.1 Hz), 7.10 (1H, dd, J=7.3, 1.0 Hz), 6.73 (1H, dd, J=7.8, 1.0 Hz), 4.69 (2H, d, J=1.5 Hz), 1.85 (2H, q, J=3.7 Hz), 1.24 (2H, q, J=3.7 Hz) ESI-MS Found: m/z [M+H] 174.

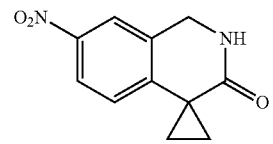 [SMILES: O=C1NCc2cc([N+](=O)[O-])ccc2C12CC2]

Step 4) Production of 7'-nitro-1',2'-dihydro-3'H-spiro[cyclopropane-1,4'-isoquinolin]-3'-one 1.3 g of potassium nitrate was gradually added to a sulfuric acid (60 mL) solution of 2.1 g of the compound obtained in the above reaction Step 3), taking 5 minutes, and further stirred at room temperature for 10 minutes. The reaction liquid was poured into ice water, the precipitated crystal was taken out through filtration, and washed with water to obtain 2.4 g of the entitled compound as a yellow solid. ¹H-NMR (CDCl$_3$) δ: 8.09 (1H, dd, J=8.8, 2.4 Hz), 8.01 (1H, t, J=2.4 Hz), 6.86 (1H, d, J=8.8 Hz), 6.30 (1H, s), 4.78 (2H, d, J=1.5 Hz), 2.01 (2H, q, J=4.1 Hz), 1.35 (2H, q, J=4.1 Hz) ESI-MS Found: m/z [M+H] 219.

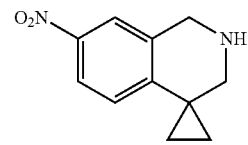 [SMILES: O=[N+]([O-])c1ccc2c(c1)CNCC21CC1]

Step 5) Production of 7'-nitro-1',2'-dihydro-3'H-spiro[cyclopropane-1,4'-isoquinoline]

With cooling with ice, 6.3 g of boron trifluoride-diethyl ether complex was added to a tetrahydrofuran suspension of 1.3 g of sodium borohydride, and stirred for 1 hour. A tetrahydrofuran (100 ml) solution of 2.4 g of the compound obtained in the above reaction Step 4) was added to the reaction liquid, and heated under reflux for 2 hours. The reaction liquid was cooled, and then neutralized with aqueous saturated sodium bicarbonate solution. The solvent was evaporated away under reduced pressure, the residue was dissolved in ethanol, 5 N hydrochloric acid was added to it, and heated under reflux for 1 hour. The reaction liquid was cooled, then the solvent was evaporated away under reduced pressure, and the residue was neutralized with aqueous potassium carbonate solution. The aqueous layer was extracted with chloroform, the organic layer was dried with anhydrous magnesium sulfate, and the solvent was evaporated away under reduced pressure to obtain the entitled compound.

ESI-MS Found: m/z [M+H] 205.

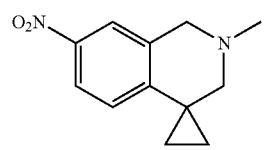 [SMILES: CN1Cc2cc([N+](=O)[O-])ccc2C2(CC2)C1]

Step 6) Production of 2'-methyl-7'-nitro-2',3'-dihydro-1'H-spiro[cyclopropane-1,4'-isoquinoline]

1.5 g of sodium cyanoborohydride was added to a methanol (50 mL) solution of the compound (2.3 g) obtained in the above reaction Step 5), 2.7 mL of aqueous 37% formaldehyde solution and 0.7 mL of acetic acid, and stirred at room temperature for 15 hours. The reaction liquid was neutralized with aqueous saturated sodium bicarbonate solution, and methanol was evaporated away under reduced pressure. The residue was diluted with water and extracted three times with chloroform. The organic layer was dried with anhydrous magnesium sulfate, the solvent was evaporated away under reduced pressure, and the crude product was purified through silica gel column chromatography (hexane/ethyl acetate) to obtain 1.7 g of the entitled compound as a colorless solid. $^1$H-NMR (CDCl3) δ: 7.97 (1H, dd, J=8.8, 2.4 Hz), 7.91 (1H, d, J=2.4 Hz), 6.78 (1H, d, J=8.8 Hz), 3.77 (2H, s), 2.57 (2H, s), 2.48 (3H, s), 1.16-1.12 (2H, m), 1.10-1.06 (2H, m) ESI-MS Found: m/z [M+H] 219.

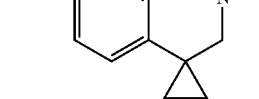

Step 7) Production of 2'-methyl-2',3'-dihydro-1'H-spiro[cyclopropane-1,4'-isoquinolin]-7'-amine 800 mg of 10% palladium-carbon was added to an ethanol (20 mL) solution of 1.7 g of the compound obtained in the above reaction Step 6), and stirred in a hydrogen atmosphere under 1 atmospheric pressure at room temperature for 15 hours. Palladium-carbon was removed through filtration, the filtrate was concentrated under reduced pressure, and the crude product was purified through basic silica gel column chromatography (hexane/ethyl acetate) to obtain 1.1 g of the entitled compound as a colorless solid. $^1$H-NMR (CDCl$_3$) δ: 6.50-6.48 (2H, m), 6.38-6.36 (1H, m), 3.61 (2H, s), 3.50 (2H, s), 2.49 (2H, s), 2.42 (3H, s), 0.91 (2H, dd, J=6.3, 4.6 Hz), 0.81 (2H, dd, J=6.3, 4.6 Hz) ESI-MS Found: m/z [M+H] 189.

Example 4

Preparation of SCH900444

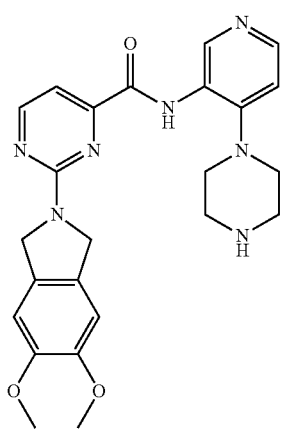 [SMILES: COc1cc2c(cc1OC)CN(c1nccc(C(=O)Nc3cnccc3N3CCNCC3)n1)C2]

Production of 2-(1,3-Dihydro-5,6-dimethoxy-2H-isoindol-2-yl)-N-[4-(1-piperazinyl)-3-pyridinyl]-4-pyrimidinecarboxamide

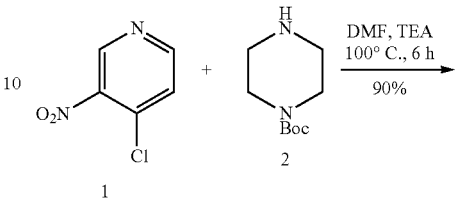

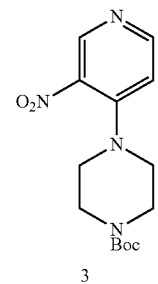

Step 1) The compound 3-Nitro-4-Chloro pyridine 1 (30.0 g, 0.19 mol) was dissolved in DMF (300 mL), tert-butyl piperazine-1-carboxylate 2 (37 g, 0.20 mol) and TEA (60.0 mL, 0.43 mol) were added. The mixture was stirred at 100° C. for 6 hours. After cooling to room temperature, the mixture was poured into ice water (2000 mL). The solid was collected by filtration and dried under air. The dried solid was taken up with EtOAc (300 mL) and stirred at room temperature for 3 hours. Yellowish solid was collected by filtration and dried under air (37 g). The mother liquid was concentrated and purified with a short silica gel column (EtOAc) to give more product 3 (15.7 g). Total 52.7 g of 3 was afforded with 90% yield.

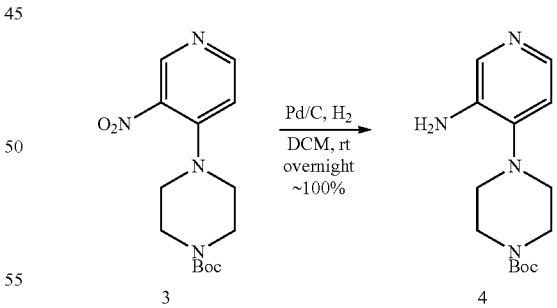

Step 2) 3-Nitro-4-boc piperizinyl pyridine 3 (37 g, 0.12 mol) was dissolved in DCM (500 mL). The resulting solution was subjected Pd/C (10%, 14.8 g) and was kept under hydrogen atmosphere at room temperature. Overnight stirring and monitored the reaction progress until the reaction is complete. The reaction solution was filtered through celite, washed with DCM/MeOH and concentrated to give the product, 4-(3-Amino-pyridin-4-yl)-piperazine-1-carboxylic acid tert-butyl ester 4 (33 g) in the yield of around 99%.

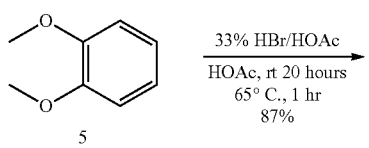

Step 3) A total of 31 mL of 33% HBr in HOAc was added to a solution of veratrole 5 (10 g, 72 mmol), paraformaldehyde (4.3 g, 144 mmol) in HOAc (43 mL) at room temperature. After stirring at rt for 20 hours, the mixture was heated to 65° C. for 1 hour, then cooled to 0° C. The solid precipitated out was collected with filtration and washed with cooled HOAc and dried under air. The mother liquid was concentrated and purified with column (Silica gel, DCM) gave more product 6. Total 20.3 g of compound 6 obtained.

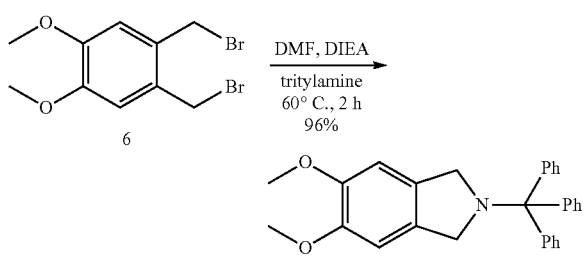

Step 4) The dibromo compound 6 (650 mg, 2.0 mmol) was dissolved in DMF (5 mL) DIEA (0.87 mL, 5.0 mmol) and tritylamine (2.1 mmol) was added and the mixture was heated to 60° C. and stirred for 2 hours. DMF was removed under vacuum and the residue was taken up with EtOAc (60 mL). The organics was washed with water and brine and dried over $Na_2SO_4$. After concentration, the residue was purified with column (silica gel, 30% EtOAc/Hexane) gave the product 7 (806 mg).

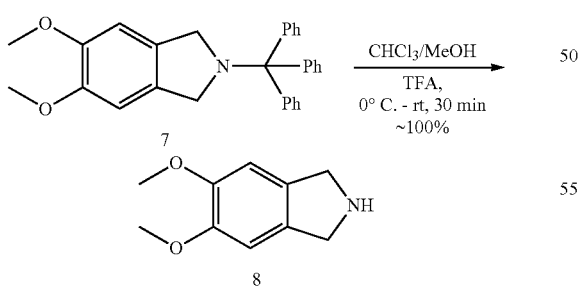

Step 5) The compound 7 (211 mg, 0.45 mmol) was dissolved in the mixture of $MeOH/CHCl_3$ (5 mL/5 mL) and cooled to 0° C. TFA (10 mL) was added carefully. After 5 minutes at 0° C., the mixture was warmed to room temperature and stirred for another 30 minutes. After concentration, the residue was taken in ether and 1 N HCl. The aqueous was extracted with ether and then basified with 4 N NaOH to pH~10. The mixture was extracted with DCM (40 mL×3). The combined organic phase were dried and concentrated. The crude product 8 (81 mg) was used in the next step directly without further purification.

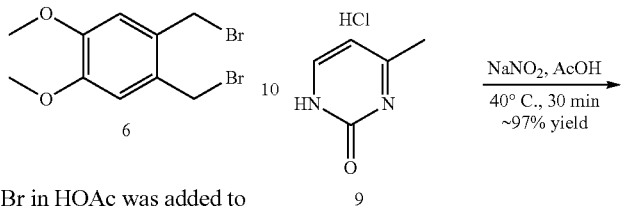

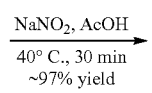

Step 6) With vigorous stirring, $NaNO_2$ (57.78 g, 0.833 mol) was added into 2-hydroxy-4-methylpyrimidine hydrochloride 9 (81.7 g, 0.556 mol) in 50% $AcOH/H_2O$ (550 mL) at 15° C. in one portion. After an exothermic reaction (~45° C.), a yellow precipitate formed. It was filtered, washed with ice-water and dried under vacuum overnight to afford the product 10 (75 g, 97%).

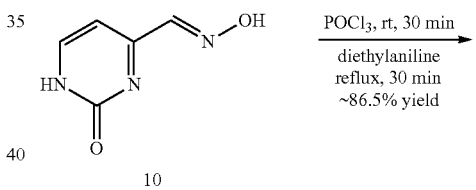

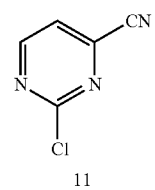

Step 7) A mixture of 2-oxo-1,2-dihydro-pyrimidine-4-carbaldehyde oxime 10 (72.6 g) in cold (0° C.) phosphorus oxychloride (280 ml) was warmed slowly with vigorous stirring until a vigorous reaction commenced, at which time warming was discontinued. Once complete dissolution had taken place, N,N-diethylaniline (36.3 mL) was added and the reaction mixture was refluxed for another 30 minutes. After cooling to room temperature, the $POCl_3$ was removed under reduced pressure and the crude was taken up with ice-water (500 mL). The mixture was extracted with DCM (5×200 mL). The combined organics was dried over $Na_2SO_4$ and concentrated. The residue was filtered through short silica gel column (washed with DCM). After concentration, the product 11 (63 g, solidified upon standing, 86.5%) was used in the next step directly.

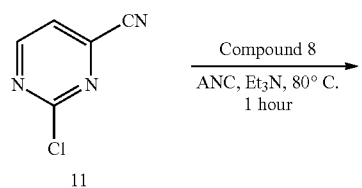

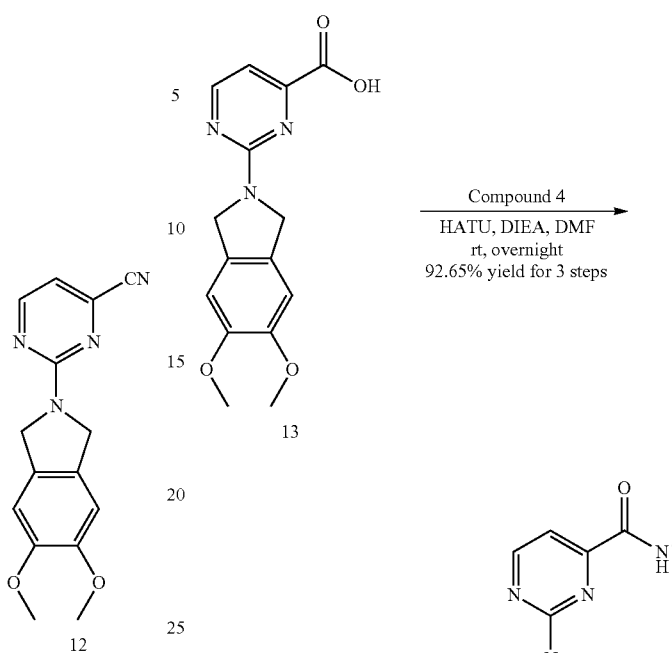

Step 8) 2-chloropyrimidine derivative 11 (5.84 g, 42.0 mmol), DIEA (8 mL, 46 mmol) and isoindoline (7.52 mg, 42.0 mmol) were dissolved in Acetonitrile (100 mL) and the mixture was heated to 80° C. and stirred for 1 hour. The solvent was removed by concentration and water was added. The solid was collected with filtration, washed with water and dried under air. The crude 12 was used in the next step directly without further purification.

Step 10) The compound, pyrimidine-4-carboxylic acid 13 (6.837 g, 22.71 mmol) was dissolved in DMF (100 mL), DIEA (3.83 mL), 3-aminopyridine building block (6.63 g, 23.85 mmol) and HATU (9.06 g, 23.85 mmol) were added at room temperature. The mixture was stirred at room temperature overnight. The mixture was poured into water (1000 mL) and the solid was collected with filtration, washed with water and dried under air. The product 14 was used in the next step directly without further purification.

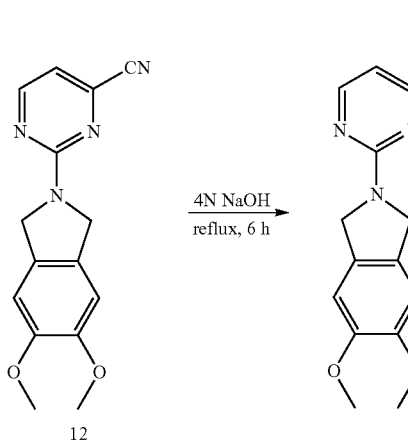

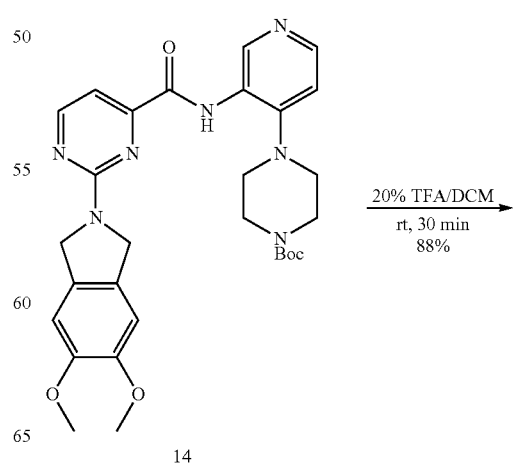

Step 9) The compound 12 (around 44 mmol) was added to 4N NaOH (140 mL) and the mixture was heated up to reflux till no starting material and amide based on LC-MS (around 6 hours). The mixture was cooled to 0° C. and the pH was adjusted to around 5 with 6N HCl. The solid precipitated out was collected with filtration, washed with water and dried under vacuum overnight. The product 13 (~12.5 g) was used in the next step directly without purification.

-continued

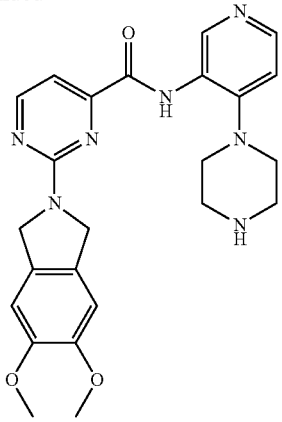

15

Step 11) The compound 14 (23.2 g) was dissolved in DCM (450 mL). TFA (100 mL was added slowly and the mixture was stirred at room temperature for 1 hour and LC-MS showed no starting material left. The solvent was removed under reduced pressure and the residue was taken with MeOH (300 mL) and 1N HCl (300 mL). The methanol and 1N HCl was removed by concentration and the residue was taken with methanol and 1N HCl again and concentrated again. To the residue, 1N HCl (100 mL) was added to dissolve the solid possibly, then MeOH (900 mL) was added and the mixture was stirred for 1 hour. The solid was collected and washed with methanol/water (9:1). The solid was taken with methanol (900 mL) and water (100 mL) again and stirred for another hour. The solid was collected with filtration and washed with methanol. After drying under vacuum, LC-MS and NMR showed the product was pure. The Product was dissolved in CAN/H$_2$O (70/30) and dried under lypholizer afforded powder 15 (20.7 g) as HCl salt. The mother liquid from filtration was concentrated and did not do further purification.

Example 5

Synergistic Combination of WEE1 Inhibitor (MK-1775) and CHK1 Inhibitor (MK-8776)

The combination of a WEE1 inhibitor (MK-1775) and a CHK1 inhibitor (MK-8776) demonstrates (i) synergistic inhibition of proliferation, (ii) synergistic induction of DNA damage, and (iii) improved anti-tumor efficacy in human cancer cell lines.
A. Combination of WEE1 and CHK1 Inhibitors Causes Synergistic Inhibition of Cell Proliferation.

Figure 1A:
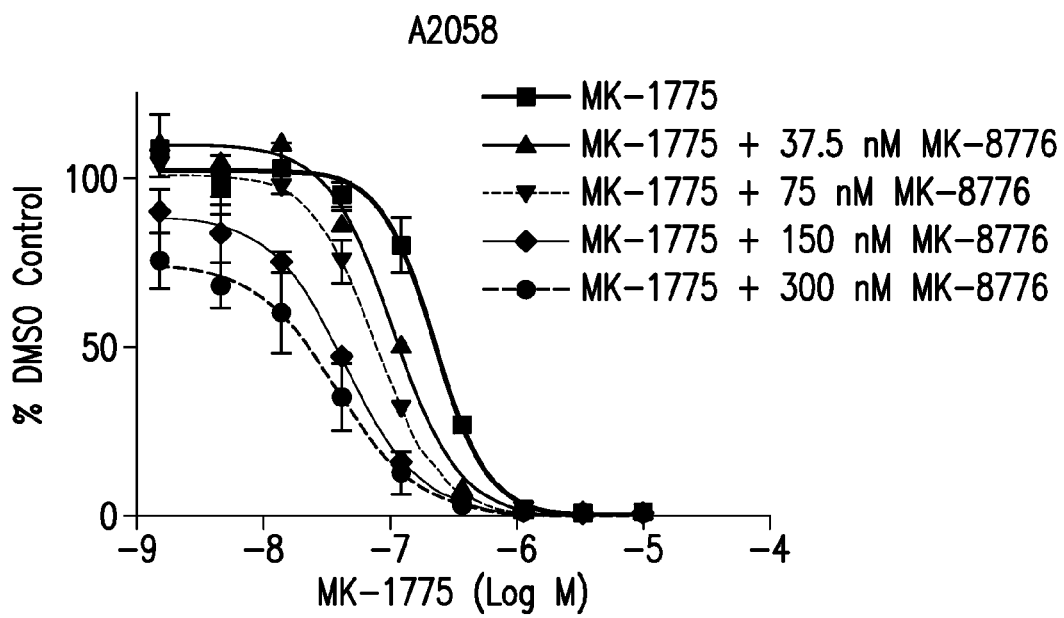
FIGS. 1A-1C are graphic illustrations of the $EC_{50}$ potency shift that demonstrated that CHK1 inhibition potentiated the anti-proliferative effect of WEE1 inhibition.
Figure 1B:
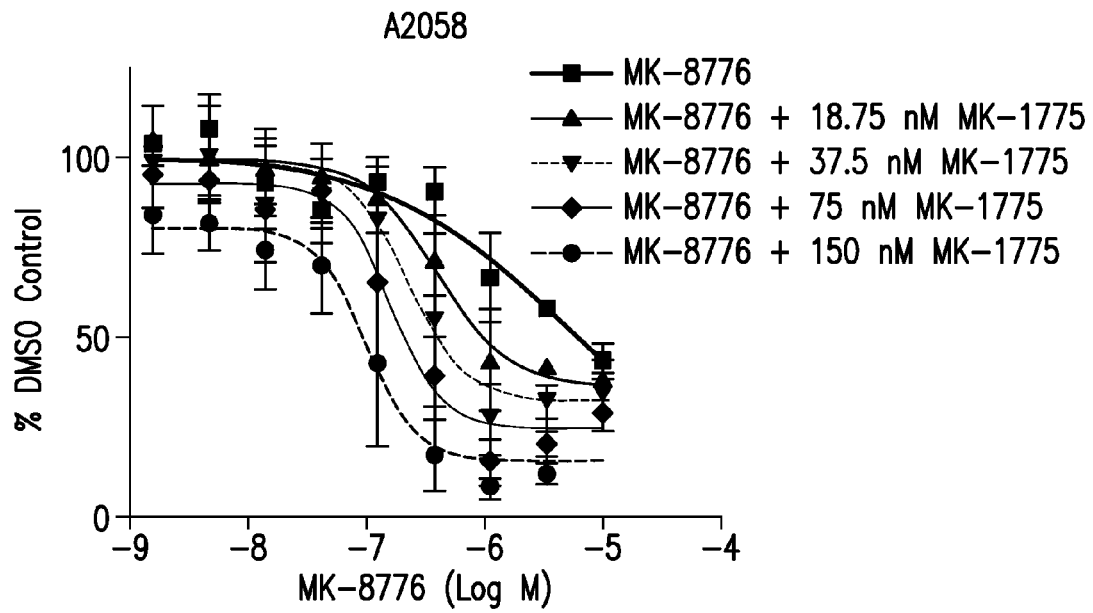

To determine the ability of each drug to potentiate the activity of the other, Applicants performed 9-point titrations of each in the added presence of increasing, but fixed, concentrations of the complimentary drug (FIGS. 1A and 1B). Analysis of cell proliferation was determined after 72 hours (3 days) incubation with either DMSO (as control) or the indicated concentrations of MK-1775 and MK-8776 by ATP vialight (Promega). Results are presented as percentage of DMSO control values. EC$_{50}$ concentrations were calculated (GraphPad Prism, GraphPad Software, San Diego, Calif.).

In the A2058 melanoma cancer cell line, MK-1775 treatment caused complete growth inhibition with an average EC$_{50}$ of 225 nM. The addition of MK-8776 at concentrations that by themselves do not effect A2058 proliferation (37.5 or 75 nM) caused a leftward shift of the MK-1775 response curve, effectively lowering the EC$_{50}$ of MK-1775. Addition of 150 nM MK-8776 reduced the MK-1775 EC$_{50}$ by 5-fold to an average of 45 nM. Similar analyses were performed in diverse cell lines where EC$_{50}$ shifts fell between 1.9- and 9.1-fold (FIG. 1A and data not shown). When the converse experiment was performed and MK-8776 was titrated over a range of fixed amounts of MK-1775 in A2058 cells, Applicants again observed leftward shifts in EC$_{50}$ curves as well as a dose-dependent increase in the maximum cell growth inhibition attained at the highest concentration of MK-8776 (FIG. 1B). These data demonstrated a robust synergistic interaction between WEE1 and CHK1 inhibitors to restrain cancer cell proliferation in a variety of tumor cell contexts.

Figure 1C:
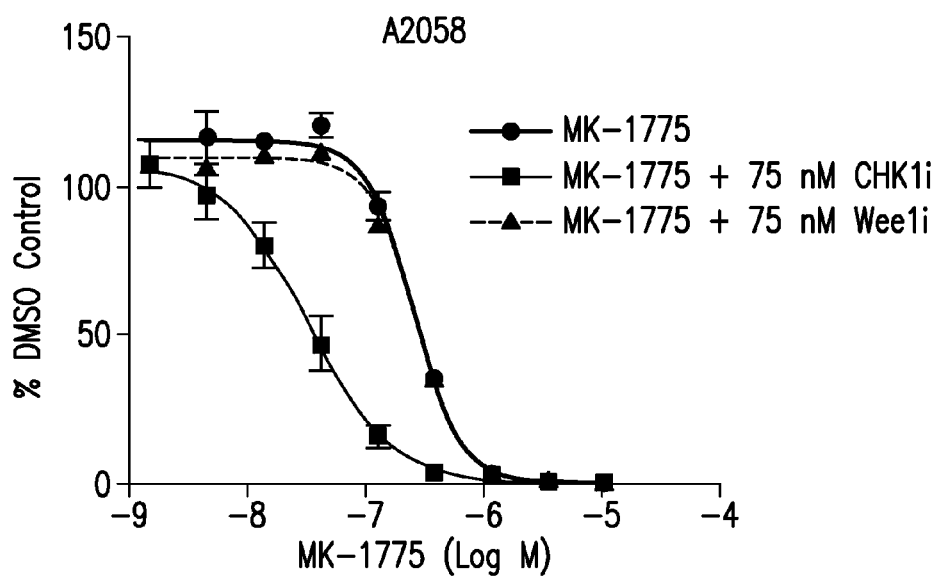
Figure 2A:
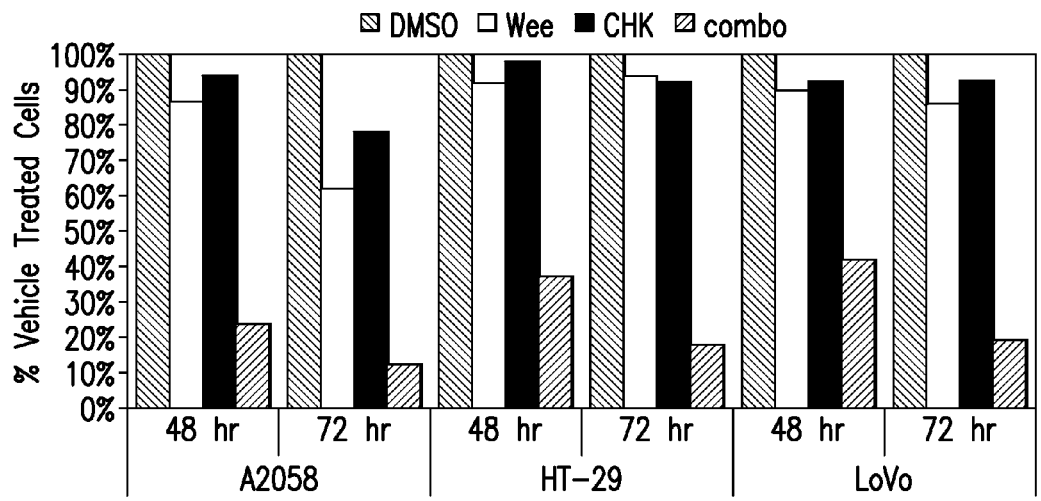
FIGS. 2A and 2B are graphic illustrations of the synergistic activity in vitro of the CHK1 and WEE1 combination to inhibit proliferation and induce DNA damage, respectively. Concentrations of a WEE1 inhibitor (MK-1775) and a CHK1 inhibitor (MK-8776) were selected that alone have a minimal effect on cell proliferation, but that when combined lead to marked inhibition of cell proliferation. Cell viability at 48 and 72 hours was measured by ATP Vialight (FIG. 2A). Analysis of DNA damage (γH2AX) by flow cytometry (FIG. 2B) at the same concentrations of MK-1775 and MK-8776 demonstrated the supra-additive effect of the combination relative to either single agent alone.
Figure 2B:
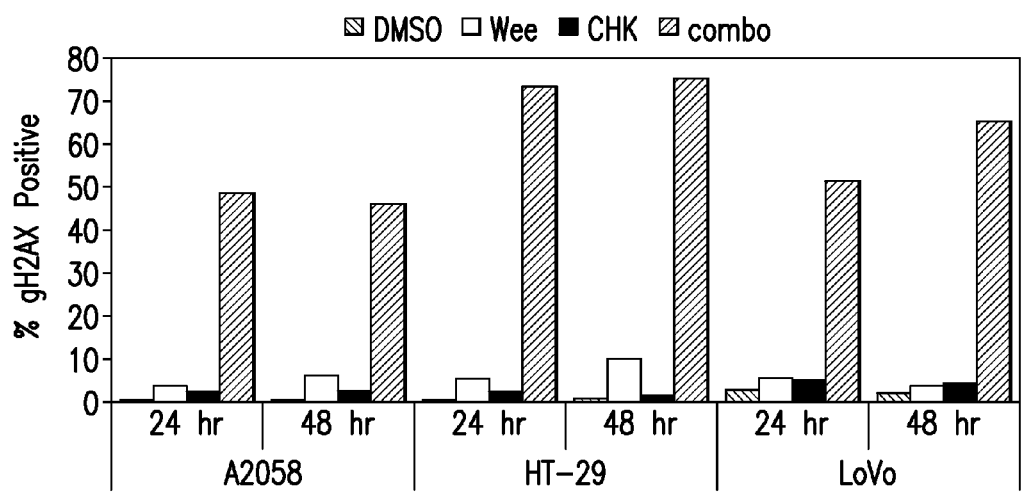

Inhibition of WEE1 and CHK1 lead to aberrant CDK1 and/or CDK2 activity, and without wishing to be bound by any theory, this is thought to underlie the potential of either target for having deleterious effects on actively dividing tumor cells. Because of the possible overlap in the MK-1775 and MK-8776 mechanisms of action, Applicants carried out sham synergy experiments. MK-1775 was titrated over 75 nM of either a WEE1 inhibitor (itself) or a CHK1 inhibitor (MK-8776) and confirmed that MK-1775 did not cause a shift in the response curve, whereas the MK-8776 caused a robust potency shift in the MK-1775 response curve (FIG. 1C). These findings support the notion of a complimentary, non-overlapping mechanism for the WEE1 and CHK1 inhibitors.
B. Inhibition of WEE1 and CHK1 Leads to Synergistic Accumulation of DNA Damage Loss of either WEE1 or CHK1 function through siRNA depletion or small molecule inhibition is reported to cause an accumulation of DNA damage. Therefore, Applicants considered the likelihood that combining MK-1775 with MK-8776 might lead to increased DNA damage. To differentiate the effect of the combination from the effect of either single agent alone, concentrations of MK-1775 and MK-8776 were selected that by themselves had negligible effect in a growth assay, but when combined led to >80% growth inhibition (FIG. 2A). Three representative cell lines that were sensitive to the MK-1775 plus MK-8776 combination were selected for analysis of DNA damage and mitotic index (data not shown). A2058 melanoma cancer cells were treated with 125 nM MK-1775, 150 nM MK-8776, or both. HT-29 colorectal cancer cells were treated with 125 nM MK-1775, 300 nM MK-8776, or both. LoVo colorectal cancer cells were treated with 40 nM MK-1775, 75 nM MK-8776, or both. FIG. 2A depicts cell proliferation and was scored at either 48 or 72 hours as the percentage of ATP ViaLight® (ViaLight® Assay, Lonza, Basel, Switzerland) of treated samples relative to DMSO treated controls. FIG. 2B depicts DNA damage and was scored at either 24 or 48 hours as the percentage of cells positive for the DNA damage marker γH2AX (histone H2AX phosphorylated at serine 139) determined by flow cytometry.

Continuous exposure to either drug alone for as long as 48 hours was unable to induce γH2AX in more than 10% of treated cells across all three cell lines. However, the same concentrations of MK-1775 and MK-8776 that demonstrated synergy in the cell growth assay also demonstrated synergy to induce γH2AX (FIG. 2B, middle panel). Combination treatment led to DNA damage (scored by γH2AX) in as many as 45% to 75% of treated cells, and was maximally induced by 24 hours. In all three cell lines, the fraction of the combination treated population containing DNA damage was in far excess of what would be predicted if the two drugs behaved in additive fashion. As an example, in LoVo cells 24 hour treatment with 40 nM MK-1775 led to detectable γH2AX in 6% of cells, treatment with 75 nM MK-8776 led to detectable γH2AX in 5% of cells, but treatment with the combination led to detectable γH2AX in 52% of cells, 41% greater than expected if the two drugs behaved additively (6%+5%=11%).

The ability of the WEE1 inhibitor (MK-1775) plus CHK1 inhibitor (MK-8776) combination to synergistically induce DNA damage was assessed in a xenograft model of human cancer. CD-1 Nu/Nu female mice aged 5-6 weeks (Charles River Laboratories) were inoculated with 5×10$^6$ LoVo cells in 100 uL (1:1 Matrigel:PBS) subcutaneously (S.C.) into the right flank. When tumor volume reached >200 mm$^3$, animals received 2 days BID dosing of either vehicle, MK-1775 (60 mpk), and/or MK-8776 (60 mpk). Three animals from each group were sacrificed via carbon dioxide inhalation at 2 hours, 24 hours, or 48 hours after the 4$^{th}$ and final dose of the 2 day BID schedule. Tumors were resected, split roughly in half, and stored in 10% formalin for immunohistochemistry (IHC) or at −80° C. for Western blot analysis.

Figure 3A:
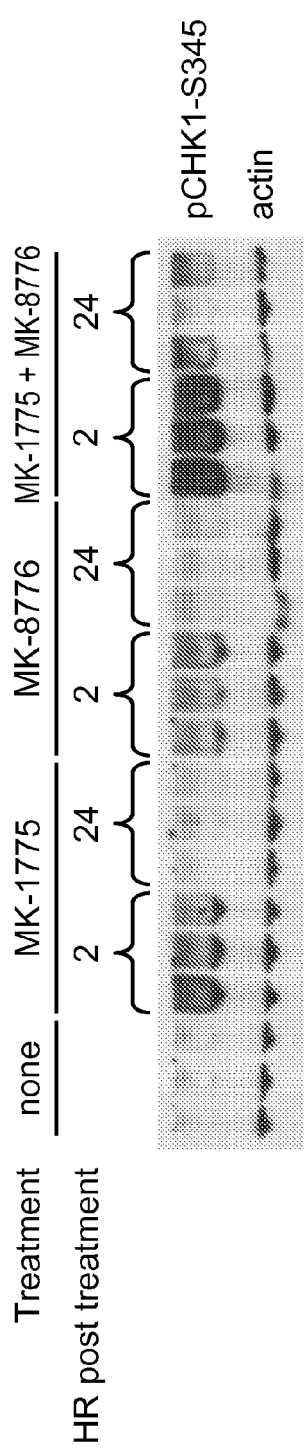
FIGS. 3A-3D are graphic illustrations of the increased and sustained DNA damage in vivo by combined CHK1 and WEE1 inhibition. LoVo xenograft tumors were treated twice daily for two days with vehicle (none), a WEE1 inhibitor (MK-1775) (60 mg/kg), a CHK1 inhibitor (MK-8776) (60 mg/kg), or both inhibitors, (MK-1775) (60 mg/kg) and MK-8776 (60 mg/kg). Tumors were harvested at 2 hours, 24 hours, and 48 hours following the final dose and analyzed by Western blot (FIG. 3A) for phosphorylated CHK1 at serine residue 345 (pCHK1$^{S345}$) or immuno-histochemistry (IHC) (FIG. 3B) for the DNA damage marker, γH2AX. Quantitative summaries of the IHC analysis for γH2AX and of the Western blot for pCHK1$^{S345}$ are shown in FIG. 3C and FIG. 3D, respectively, on LoVo xenograft tumors.

FIG. 3A shows a Western blot analysis of phosphorylated CHK1 at serine 345 (pCHK1$^{S345}$), which marks an activated DNA damage response. When dosed alone, MK-1775 and MK-8776 both lead to a transient increase of pCHK1$^{s345}$ at 2 hours after the final dose, though this effect is lost by 24 hours after the final dose. Notably, treatment with the combination resulted in a greater induction of pCHK1$^{S345}$ at 2 hours, and this effect was still evident at 24 hours post-final dose. Consistent with this observation, IHC results in FIG. 3B demonstrated an increase of the DNA damage marker γH2AX when the combination was used, relative to either single agent alone. Quantitation of the IHC results in FIGS. 3C and 3D shows that this is true of both the short term intensity (2 hours) as well as the duration of the γH2AX (FIG. 3C) signal (out to 48 hours post final dose) and pCHK1$^{S345}$.

C. Inhibition of Both WEE1 and CHK1 Improves Anti-Tumor Efficacy of Either Agent Administered Alone in a Xenograft Model of Human Colorectal Carcinoma.

Figure 3B:
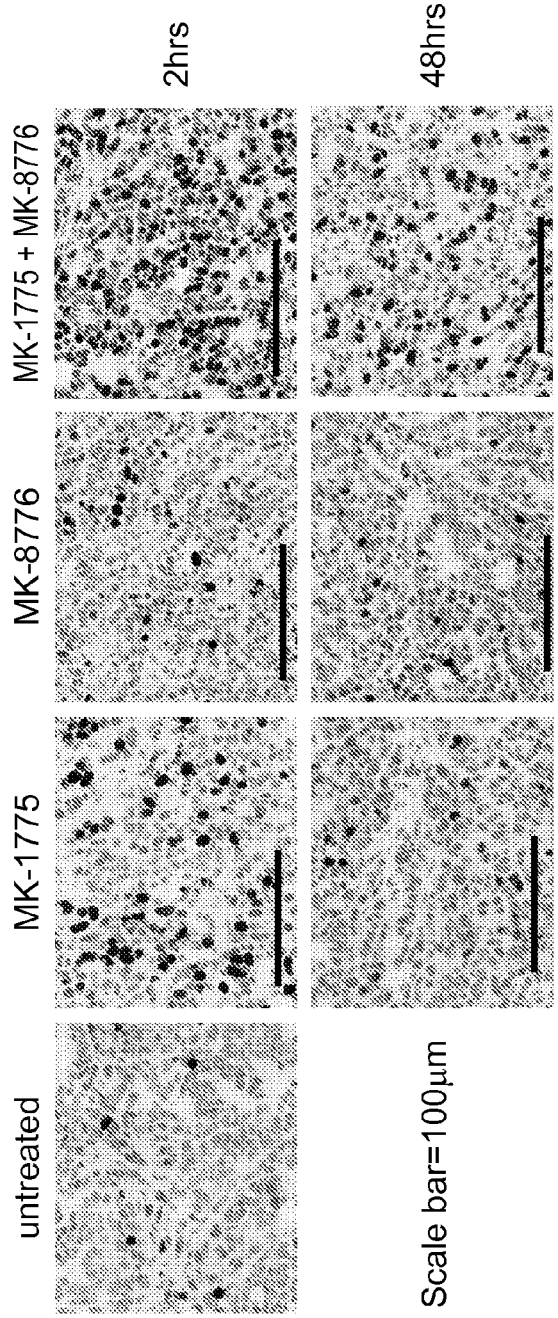
Figure 3C:
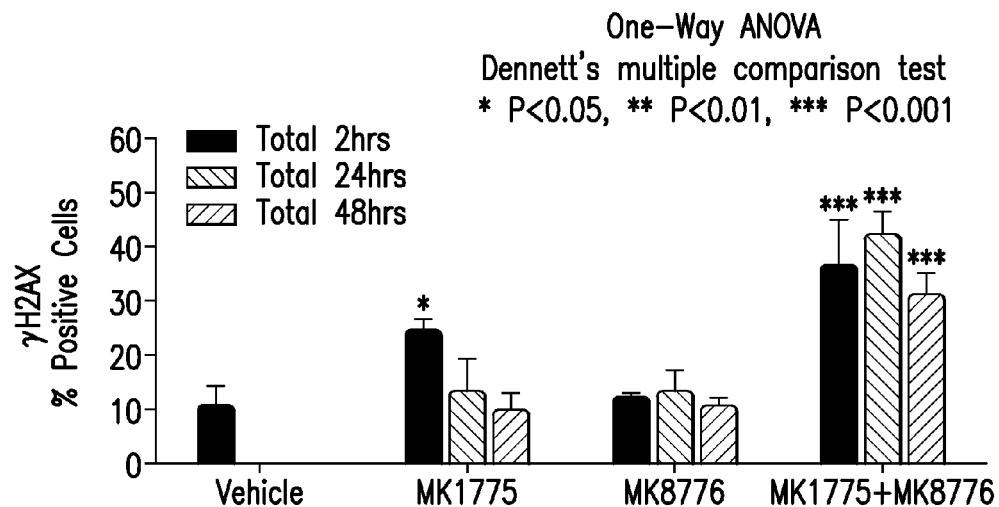
Figure 3D:
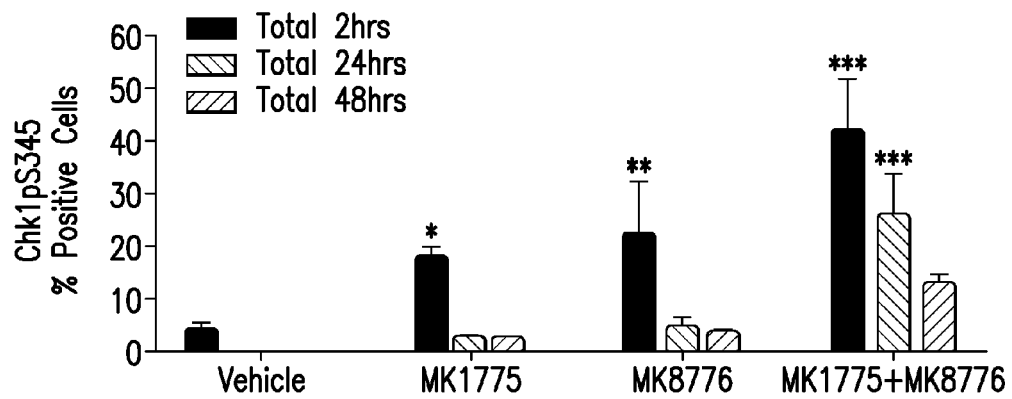

Combination of the WEE1 inhibitor (MK-1775) and CHK1 inhibitor (MK-8776) synergistically induces DNA damage both in vitro (FIGS. 2A and 2B) and in vivo (FIG. 3A-3C). The anti-tumor efficacy of this combination was assessed in a xenograft model of human colorectal cancer. CD-1 Nu/Nu female mice aged 5-6 weeks (Charles River Laboratories) were inoculated with 5×10$^6$ LoVo cells in 100 uL (1:1 Matrigel:PBS) S.C. into the right flank. When tumor volume reached 200 mm$^3$ (+/−50) mice were pair-matched so each treatment group (n=10) had a similar mean tumor volume and standard deviation. Tumor volume and body weights were recorded bi-weekly. Data presented in FIG. 4 were through study day 18, after animals had received 3 treatment cycles, each consisting of 2 day BID dosing of (i) vehicle only, (ii) MK-1775 (50 mpk) plus vehicle, (iii) MK-8776 (50) plus vehicle, or (iv) MK-1775 (50 mpk) plus MK-8776 (50 mpk).

Treatment of the LoVo xenograft tumors with MK-1775 alone had a modest effect on growth, resulting in 42% T/C (calculated as 100*ΔT/ΔC if ΔT>0, or as 100*ΔT/Ti if ΔT<0, where ΔT=final mean volume−initial mean volume of treated group, AC=final mean volume−initial mean volume of vehicle control group, and Ti=initial mean volume of treated group). Similarly, treatment with MK-8776 alone had a modest effect on tumor growth, resulting in 52% T/C. However, the combination of MK-1775 and MK-8776, at the same doses and schedules that were used for either single agent, resulted in 14% tumor regression. This data support the claim that combined inhibition of WEE1 and CHK1 has greater anti-tumor efficacy than either drug alone, and highlights the potential of this unique drug combination in the treatment of human neoplasms.

What is claimed is:

1. A method of treating a cancer, selected from the group consisting of breast cancer, melanoma, colorectal cancer, non-small cell lung cancer, and ovarian cancer, with a WEE1 inhibitor and a CHK1 inhibitor, wherein the WEE1 inhibitor is MK-1775 or a pharmaceutically acceptable salt thereof, and the CHK1 inhibitor is MK-8776 or a pharmaceutically acceptable salt thereof.

2. A method of claim 1 for treating a cancer patient, in need of treatment thereof, comprising administering to said patient a therapeutically effective amount of said WEE1 inhibitor and said CHK1 inhibitor.

3. The method of claim 2 wherein the WEE1 inhibitor is administered in a dose between 100 mg per day and 250 mg per day.

4. The method of claim 3 wherein the WEE1 inhibitor is administered five times, over the course of two and a half days.

5. The method of claim 3 wherein the WEE1 inhibitor is administered once a day, over the course of two days.

6. The method of claim 2 wherein the CHK1 inhibitor is administered in a dose between 100 mg per day and 200 mg per day.

7. The method of claim 6 wherein the CHK1 inhibitor is administered once a day, over the course of two days.

* * * * *